United States Patent
Michaelis et al.

(10) Patent No.: US 7,462,638 B2
(45) Date of Patent: Dec. 9, 2008

(54) USE OF IκB-KINASE INHIBITORS IN PAIN THERAPY

(75) Inventors: Martin Michaelis, Frankfurt (DE); Olaf Ritzeler, Bad Soden (DE); Gerhard Jaehne, Frankfurt (DE); Karl Rudolphi, Mainz (DE); Gerd Geisslinger, Bad Soden (DE); Hans-Georg Schaible, Jena (DE)

(73) Assignee: SANOFI-AVENTIS Deutschland GmbH, Frankfurt am Main (DE)

( * ) Notice: Subject to any disclaimer, the term of this patent is extended or adjusted under 35 U.S.C. 154(b) by 277 days.

(21) Appl. No.: 10/642,974

(22) Filed: Aug. 18, 2003

(65) Prior Publication Data

US 2004/0116494 A1    Jun. 17, 2004

Related U.S. Application Data

(60) Provisional application No. 60/434,628, filed on Dec. 19, 2002.

(30) Foreign Application Priority Data

Aug. 17, 2002    (DE)    ................................. 102 37 723

(51) Int. Cl.
*A61K 31/4184*    (2006.01)

(52) U.S. Cl. ...................................... 514/394; 514/414
(58) Field of Classification Search ................. 514/447, 514/443, 393, 394, 396, 415–419
See application file for complete search history.

(56) References Cited

U.S. PATENT DOCUMENTS

| | | |
|---|---|---|
| 6,358,978 B1 | 3/2002 | Ritzeler et al. |
| 6,627,637 B2 | 9/2003 | Ritzeler et al. |
| 2003/0119820 A1 | 6/2003 | Ritzeler et al. |

OTHER PUBLICATIONS

U.S. Appl. No. 10/642,970, filed Aug. 18, 2003.*
U.S. Appl. No. 60/570,146, filed May 12, 2004.*
U.S. Appl. No. 10/842,427, filed May 11, 2004.*
Hottelet, et al., Development of IkB Kinase Inhibitors As Anti-Inflammatory Therapeutics, Inflammation Research Supplemental, p. 2, (2000), S91, XP009023847.
Yin, et al., The Anti-Inflammatory Agents Aspirin And Salicylate Inhibit The Activity of IkB Kinase-Beta, Nature, MacMillan Journals Ltd. vol. 39615, pp. 77-80, (1998), XP002938591.

* cited by examiner

*Primary Examiner*—Brian-Yong S Kwon
(74) *Attorney, Agent, or Firm*—James W. Bolcsak

(57) ABSTRACT

The present invention relates to the use of IκB-kinase Inhibitors and methods for the prophylaxis and therapy for treating pain comprising administering such compounds.

3 Claims, No Drawings

USE OF IκB-KINASE INHIBITORS IN PAIN THERAPY

This application claims the benefit of U.S. Provisional Application No. 60/434,628, filed Dec. 19, 2002. The content of U.S. Provisional Application 60/434,628 is incorporated herein by reference.

FIELD OF THE INVENTION

The invention relates to the use of IκB-kinase inhibitors for treating pain.

BACKGROUND OF THE INVENTION

Patent applications WO 01/00610, WO 01/30774 and WO 01/68648, the content of each of which is incorporated herein by reference, describe compounds which are able to modulate NFκB. NFκB is a heterodimeric transcription factor which is able to activate a large number of genes which encode, inter alia, proinflammatory cytokines such as IL-1, IL-2, TNFα or IL-6. NFκB is present in the cytosol of cells, where it is complexed with its naturally occurring inhibitor IκB. Stimulation of the cells, for example by cytokines, leads to the IκB being phosphorylated and subsequently broken down proteolytically. This proteolytic breakdown leads to the activation of NFκB, which then migrates into the nucleus of the cell, where it activates a large number of proinflammatory genes.

In diseases such as rheumatoid arthritis (in connection with inflammation), osteoarthritis, asthma, cardiac infarction, Alzheimer's diseases or atherosclerosis, NFκB is activated to beyond the normal extent. The inhibition of NFκB is also of value in the treatment of cancer since it is used in such treatment to augment the cytostatic therapy. It has been demonstrated that pharmaceuticals such as glucocorticoids, salicylates or gold salts, which are used in the therapy of rheumatism, inhibit the NFκB-activating signal chain at various points or interfere directly with the transcription of the genes. The first step in said signal cascade is the breakdown of IκB. This phosphorylation is regulated by the specific IκB kinase.

Pharmaceuticals belonging to a large number of different substance groups are employed in treating acute and chronic pain. Despite this, the therapy of pain has still not been satisfactorily solved even today. This is due, in particular, to the fact that the analgesics which are on the market do not have a sufficiently powerful effect.

In an endeavor to obtain active compounds for treating pain, it has now been found that it is possible to use IκB-kinase inhibitors for this purpose. In particular, it has been possible to demonstrate, in the models employed, a strength of effect which is clearly superior to that of classical nonsteroidal anti-inflammatory agents.

The invention relates, therefore, to the use of IκB-kinase inhibitors for producing pharmaceuticals for treating pain.

The term "pain" is understood as meaning acute pains and chronic pains. The following are examples of chronic pains: chronic musculoskeletal diseases, such as back pains,
pains associated with menstrual bleeding,
pains associated with osteoarthritis or rheumatoid arthritis,
pains associated with intestinal inflammation,
pains associated with cardiac muscle inflammation,
pains associated with multiple sclerosis,
pains associated with neuritis,
pains associated with carcinomas and sarcomas,
pains associated with AIDS,
pains associated with chemotherapy,
amputation pain,
trigeminus neuralgia,
headaches, such as migraine cephalalgia, or
neuropathic pains, such as post-herpes zoster neuralgia.

The following are examples of acute pains:
pains following injuries,
post-operative pains,
pains in association with an acute attack of gout, or
acute pains following jaw-bone surgery interventions.

Examples of IκB-kinase inhibitors are indole derivatives or benzimidazole derivatives as are described in the patent applications WO 01/00610 and WO 01/30774.

SUMMARY OF THE INVENTION

The invention furthermore relates to the use of compounds of the formula I

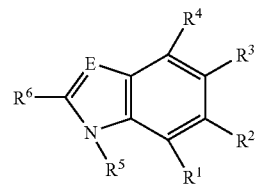

(I)

and/or a stereoisomeric form of the compound of the formula I and/or a physiologically tolerated salt of the compound of the formula I, for producing pharmaceuticals for treating pains, where E is N atom or the radical —C($R^{19}$)—, where $R^{19}$ is hydrogen atom or the radical $R^9$, one of the substituents $R^1$, $R^2$, $R^3$ and $R^4$ is a radical of the formula II,

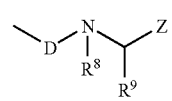

(II)

in which D is —C(O)—, —S(O)— or —S(O)$_2$—,
$R^8$ is hydrogen atom or —($C_1$-$C_4$)-alkyl,
$R^9$ is 1. characteristic radical of an amino acid,
2. aryl, in which aryl is unsubstituted or substituted,
3. heteroaryl having from 5 to 14 ring members, in which heteroaryl is unsubstituted or substituted,
4. heterocycle having from 5 to 12 ring members, in which heterocycle is unsubstituted or substituted,
5. —($C_1$—$C_6$)-alkyl, in which alkyl is straight-chain or branched and is unsubstituted or substituted, once, twice or three times, independently of each other, by
  5.1 aryl, in which aryl is unsubstituted or substituted,
  5.2 heteroaryl having from 5 to 14 ring members, in which heteroaryl is unsubstituted or substituted,
  5.3 heterocycle having from 5 to 12 ring members, in which heterocycle is unsubstituted or substituted,
  5.4 —O—$R^{11}$,
  5.5 =O,
  5.6 halogen,
  5.7 —CN,
  5.8 —$CF_3$,
  5.9 —S(O)$_x$—$R^{11}$, in which x is the integer zero, 1 or 2,
  5.10 —C(O)—O—$R^{11}$, 5.11 —C(O)—N($R^{11}$)$_2$,
5.12 —C(O)—$R^{11}$,
5.13 —N($R^{11}$)$_2$,
5.14 —(C$_3$-C$_6$)-cycloalkyl,
5.15 radical of the formula

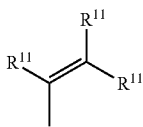

or 5.16 radical of the formula

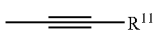

$R^{11}$ is a) hydrogen atom,
  b) (C$_1$-C$_6$)-alkyl, in which alkyl is unsubstituted or substituted once, twice or three times
    1. aryl, in which aryl is unsubstituted or substituted,
    2. heteroaryl having from 5 to 14 ring members,
    3. heterocycle having from 5 to 12 ring members,
    4. halogen,
    5. —N—(C$_1$-C$_6$)$_n$-alkyl, in which n is the integer zero, 1 or 2 and alkyl is unsubstituted or substituted once, twice or three times, independently of each other, by halogen or by —C(O)—OH,
    6. —O—(C$_1$-C$_6$)-alkyl or
    7. —C(O)—OH,
  c) aryl, in which aryl is unsubstituted or substituted,
  d) heteroaryl having from 5 to 14 ring members, or
  e) heterocycle having from 5 to 12 ring members, and, in the case of ($R^{11}$)$_2$, $R^{11}$ has, independently of each other, the meanings of a) to e), Z is 1. aryl, in which aryl is unsubstituted or substituted,
  2. heteroaryl having from 5 to 14 ring members, in which heteroaryl is unsubstituted or substituted,
  3. heterocycle having from 5 to 12 ring members, in which heterocycle is unsubstituted or substituted,
  4. —(C$_1$-C$_6$)-alkyl, in which alkyl is substituted or unsubstituted
  5. —C(O)—$R^{11}$,
  6. —C(O)—O—$R^{11}$ or
  7 —C(O)—N($R^{11}$)$_2$, or $R^8$ and $R^9$ form, together with the nitrogen atom and carbon atom to which they are in each case bonded, a heterocyclic ring of the formula IIa,

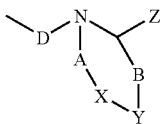

in which D and Z are defined as in formula II,
  A is nitrogen atom or the radical —CH$_2$—,
  B is oxygen atom, sulfur atom, nitrogen atom or the radical —CH$_2$—,
  X is oxygen atom, sulfur atom, nitrogen atom or the radical —CH$_2$—,
  Y is absent or is oxygen atom, sulfur atom, nitrogen atom or the radical —CH$_2$—, or
  X and Y together form a phenyl, 1,2-diazine, 1,3-diazine, or 1,4-diazine radical, where the ring system which is formed by N, A; X, Y, B and carbon atom does not contain more than one oxygen atom, X is not oxygen atom, sulfur atom or nitrogen atom when A is nitrogen atom, does not contain more than one sulfur atom, and contains 1, 2, 3 or 4 nitrogen atoms, and where an oxygen atom and a sulfur atom are not present simultaneously, where the ring system which is formed by N, A, X, Y, B and carbon atom is unsubstituted or is substituted, once, twice or three times, independently of each other, by (C$_1$-C$_8$)-alkyl, in which alkyl is unsubstituted or substituted, once or two times, by
  1.1. —OH,
  1.2. —(C$_1$-C$_8$)-alkoxy,
  1.3. halogen,
  1.4. —NO$_2$,
  1.5. —NH$_2$,
  1.6. —CF$_3$,
  1.7. methylenedioxyl,
  1.8 —C(O),
  1.9. —C(O)—CH$_3$,
  1.10. —(C$_1$-C$_4$)-alkoxycarbonyl,
  1.11. —CN,
  1.12. —C(O)—OH,
  1.13. —C(O)—NH$_2$,
  1.14. tetrazolyl,
  1.15. phenyl,
  1.16. phenoxy,
  1.17. benzyl or
  1.18. benzyloxy or $R^9$ and Z form, together with the carbon atoms to which they are in each case bonded, a heterocyclic ring of the formula IIc,

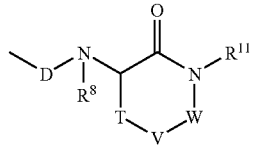

in which D, $R^8$ and $R^{11}$ are defined as in formula II,
  T is oxygen atom, sulfur atom, nitrogen atom or the radical —CH$_2$—,
  W is oxygen atom, sulfur atom, nitrogen atom or the radical —CH$_2$—,
  V is absent or is oxygen atom, sulfur atom, nitrogen atom or the radical —CH$_2$—, or
  T and V or V and W together form a phenyl, 1,2-diazine, 1,3-diazine or 1,4-diazine radical, where the ring system which is formed by N, T, V, W and two carbon atoms does not contain more than one oxygen atom, does not contain more than one sulfur atom and contains 1, 2, 3 or 4 nitrogen atoms, where an oxygen atom and a sulfur atom are not present simultaneously, and where the ring system which is formed by N, T, V, W and two carbon atoms is unsubstituted or is substituted, once, twice or three times, independently of each other, by the substituents which are defined above under 1.1. to 1.18., and the other substituents $R^1$, $R^2$, $R^3$ and $R^4$ in each case are, independently of each other,
1. hydrogen atom,
2. halogen,
3. —$(C_1-C_6)$-alkyl,
4. heteroaryl having from 5 to 14 ring members, in which heteroaryl is unsubstituted or substituted,
5. heterocycle having from 5 to 12 ring members, in which heterocycle is unsubstituted or substituted,
6. —$NO_2$,
7. —CN,
8. —O—$(C_O-C_4)$-alkylaryl,
9. —O—$(C_1-C_4)$-alkyl,
10. —O—$R^{11}$,
11. —$N(R^{11})_2$,
12. —$S(O)_r$—$R^{11}$, in which r is the integer zero, 1 or 2, or
13. —$CF_3$, $R^5$ is 1. hydrogen atom,
2. —OH or
3. =O, and $R^6$ is 1. aryl, in which aryl is unsubstituted or substituted,
2. phenyl which is substituted once or twice by
  2.1 —CN,
  2.2 —$NO_2$,
  2.3 —O—$(C_1-C_4)$-alkyl,
  2.4 —$N(R^{11})_2$,
  2.5 —NH—C(O)—$R^{11}$,
  2.6 —$S(O)_s$—$R^{11}$, in which s is the integer zero, 1 or 2,
  2.7 —C(O)—$R^{11}$ or
  2.8 —$(C_1-C_4)$-alkyl-$NH_2$,
3. heteroaryl having from 5 to 14 ring members, is unsubstituted or is substituted once, twice or three times, or
4. heterocycle having from 5 to 12 ring members, is unsubstituted or is substituted once, twice or three times.

The invention furthermore relates to the use, according to the invention, of the compound of the formula I, where
E is N atom or the radical —$C(R^{19})$—,
  where $R^{19}$ is hydrogen atom or the radical $R^9$, one of the substituents $R^1$, $R^2$, $R^3$ and $R^4$ is a radical of the formula II, in which
D is —C(O)—, —S(O)— or —$S(O)_2$—,
$R^8$ is hydrogen atom or —$(C_1-C_4)$-alkyl,
$R^9$ is 1. a characteristic radical of an amino acid which is derived from a naturally occurring □-amino acid of the group alanine, valine, leucine, isoleucine, phenylalanine, tyrosine, tryptophan, serine, threonine, cysteine, methionine, asparagine, glutamine, lysine, histidine, arginine, glutamic acid and aspartic acid,
2. a characteristic radical of an amino acid which is derived from an amino acid which is not naturally occurring, such as 2-aminoadipic acid, 2-aminobutyric acid, 2-aminoisobutyric acid, 2,4-diaminobutyric acid, 2,3-diaminopropionic acid, 1,2,3,4,-tetrahydroisoquinoline-1-carboxylic acid, 1,2,3,4-tetrahydroisoquinoline-3-carboxylic acid, 2-aminopimelic acid, 3-(2-thienyl)alanine, 3-(3-thienyl)alanine, sarcosine, pipecolic acid, 2-aminoheptanoic acid, hydroxylysine, N-methylisoleucine, 6-N-methyllysine, norleucine, N-methylvaline, norvaline, ormithine, allo-isoleucine, 4-hydroxyproline, allo-hydroxylysine, allo-threonine, 3-hydroxyproline, 3-(2-naphthyl)alanine, 3-(1-naphthyl)alanine), homocysteine, homophenylalanine, homocysteic acid, 2-amino-3-phenylaminoethylpropionic acid, 2-amino-3-phenylaminopropionic acid, homotryptophan, cysteic acid, 3-(2-pyridyl)alanine, 3-(3-pyridyl)alanine, 3-(4-pyridyl)alanine, phosphinothricin, 4-fluorophenylalanine, 3-fluorophenylalanine, 2-fluorophenylalanine, 4-chlorophenylalanine, 4-nitrophenylalanine, cyclohexylalanine, 4-aminophenylalanine, citrulline, 5-fluorotryptophan, 5-methoxytryptophan, methionine sulfone, methionine sulfoxide or —NH—$NR^{11}$—CON$(R^{11})_2$, in which $R^{11}$ is defined as below,
3. aryl, from the group anthryl, biphenylyl, 2-biphenylyl, 3-biphenylyl, 4-biphenylyl, fluorenyl, naphthyl, 1-naphthyl, 2-naphthyl or phenyl, in which aryl is unsubstituted or substituted once, twice or three times by identical or different radicals from the series —C(O)—$(C_1-C_4)$-alkyl, —C(O), =O, —NH—$(C_1-C_4)$-alkyl, —NH—$((C_1-C_4)$-alkyl$)_2$, —$(C_1-C_8)$-alkyl, —$(C_1-C_8)$-alkoxy, halogen, nitro, amino, trifluoromethyl, hydroxyl, —$CF_3$, hydroxy-$(C_1-C_4)$-alkyl, such as hydroxymethyl or 1-hydroxyethyl or 2-hydroxyethyl, methylenedioxy, ethylenedioxy, formyl, acetyl, cyano, hydroxycarbonyl, aminocarbonyl, —$(C_1-C_4)$-alkoxycarbonyl, phenyl, phenoxy, benzyl, benzyloxy, —$S(O)_x$—$R^{11}$ in which x is the integer zero, 1 or 2, —O—$(C_1-C_4)$-alkyl, —C(O)—OH, —C(O)—O—$(C_1-C_4)$-alkyl, —NH—C(O)—$(C_1-C_4)$-alkyl or tetrazolyl,
4. heteroaryl having from 5 to 14 ring members, in which heteroaryl is unsubstituted or substituted and, as a radical, is derived from the group azepine, azetidine, benzimidazole, benzodioxolane, 2-benzofuran, benzothiazole, benzothiophene, 2-benzothiophene, 2-benzoxazole, β-carboline, quinoxaline, quinazoline, quinoline, 2-quinoxaline, cyclohepta[b]-5-pyrrole, diazepine, dihydropyridine, 3-hydroxypyrro-2,4-dione, imidazole, 4-imidazole, imidazolidine, imidazoline, indazole, indole, isoquinoline, isoindole, isothiazole, isothiazolidine, isoxazole, 2-isoxazolidine, isoxazolidine, isoxazolone, methylimidazole, 3-(N-methylpyrrolidine), morpholine, oxazole, 1,3,4-oxadiazole, oxadiazolidinedione, oxadiazolone, 5-oxo-4,5-dihydro-[1,3,4]oxadiazole, 5-oxo-1,2,4-thiadiazole, 1,2,3,5-oxathiadiazole-2-oxide, 1-oxo-1,2-dihydro-3-isoquinol, phenylpyrrole, 5-phenyl-2-pyrrole, phthalazine, piperazine, piperidine, pyrazine, pyrazole, pyrazoline, pyrazolidine, pyrazoline, pyridazine, pyrimidine, pyridine, pyridyl-N-oxide, 2-pyrrole, 3-pyrrole, pyrrolidine, pyrroline, 4,5,6,7-tetrahydro-2-indole, tetrahydrothienyl, tetrazole, thiadiazole, thiazole, thiomorpholine, thiophene, triazole, triazolone or triazole,
in which heteroaryl is unsubstituted or substituted once, twice or three times by identical or different radicals which are derived from the series —C(O)—$(C_1-C_4)$-alkyl, —C(O), =O, —NH—$(C_1-C_4)$-alkyl, —NH—$((C_1-C_4)$-alkyl$)_2$, —$(C_1-C_8)$-alkyl, —$(C_1-C_8)$-alkoxy, halogen, nitro, amino, trifluoromethyl, hydroxyl, —$CF_3$, hydroxy-$(C_1-C_4)$-alkyl such as hydroxymethyl or 1-hydroxyethyl or 2-hydroxyethyl, methylenedioxy, ethylenedioxy, formyl, acetyl, cyano, hydroxycarbonyl, aminocarbonyl, —$(C_1-C_4)$-alkoxycarbonyl, phenyl, phenoxy, benzyl, benzyloxy, —$S(O)_x$—$R^{11}$, in which x is the integer zero, 1 or 2, —O—$(C_1-C_4)$-alkyl, —C(O)—OH, —C(O)—O—$(C_1-C_4)$-alkyl, —NH—C(O)—$(C_1-C_4)$-alkyl or tetrazolyl,
5. —$(C_1-C_6)$-alkyl in which alkyl is straight-chain or branched and is unsubstituted or substituted once, twice or three times, independently of each other, by
  5.1 aryl, in which aryl is defined as above,
  5.2 heteroaryl having from 5 to 14 ring members, in which heteroaryl is defined as above, 5.3 —$(C_3-C_6)$-cycloalkyl,
5.4 —O—$R^{11}$,
5.5 =O,
5.6 halogen,
5.7 —CN,
5.8 —$CF_3$,
5.9 —$S(O)_x R^{11}$, in which x is the integer zero, 1 or 2,
5.10 —C(O)—O—$R^{11}$,
5.11 —C(O)—$N(R^{11})_2$,
5.12 —C(O)—$R^{11}$,
5.13 —$N(R^{11})_2$,
5.14 a radical of the formula

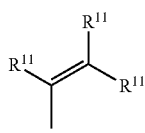

or
5.15 a radical of the formula

in which
$R^{11}$ is a) hydrogen atom,
b) $(C_1-C_6)$-alkyl in which alkyl is unsubstituted or substituted once, twice or three times by
1. aryl, in which aryl is defined as above,
2. heteroaryl having 5 to 14 ring members, in which heteroaryl is defined as above,
3. halogen,
4. —N—$(C_1-C_6)_n$-alkyl, in which n is the integer zero, 1 or 2 and alkyl is unsubstituted or substituted once, twice or three times, independently of each other, by halogen or by —C(O)—OH,
5. —O—$(C_1-C_6)$-alkyl or
6. —C(O)—OH,
c) aryl, in which aryl is defined as above, or
d) heteroaryl having from 5 to 14 ring members, in which heteroaryl is defined as above, and
in the case of $(R^{11})_2$, the radical $R^{11}$ has, independent of each other, the meaning of a) to d),
Z is 1. aryl in which aryl is defined as above,
2. heteroaryl having from 5 to 14 ring members, in which heteroaryl is defined as above,
3. —$(C_1-C_6)$-alkyl, in which alkyl is straight-chain or branched and is substituted once or twice by phenyl or —OH,
4. —C(O)—O—$R^{11}$, or
5. —C(O)—$N(R^{11})_2$, and the other substituents $R^1$, $R^2$, $R^3$ and $R^4$ in each case are, independently of each other,
1. hydrogen atom,
2. halogen,
3. —$(C_1-C_4)$-alkyl,
4. heteroaryl having from 5 to 14 ring members, in which heteroaryl is as defined above,
5. —$(C_1-C_6)$-alkyl,
6. —$NO_2$,
7. —CN,
8. —O—$(C_0-C_4)$-alkyl-aryl, in which aryl is defined as above,
9. —O—$(C_1-C_4)$-alkyl,
10. —$OR^{11}$,
11. —$N(R^{11})_2$,
12. —$S(O)_x—R^{11}$, in which x is the integer zero, 1 or 2, or
13. —$CF_3$,
$R^5$ is 1. hydrogen atom,
2. —OH, or
3. =O, and
$R^6$ is 1. aryl, from the group naphthyl, 1-naphthyl, 2-naphthyl, phenyl, biphenylyl, 2-biphenylyl, 3-biphenylyl, 4-biphenylyl, anthryl or fluorenyl,
in which aryl is unsubstituted or substituted, once, twice or three times, by identical or different radicals from the series —C(O)—$(C_1-C_4)$-alkyl, —C(O), =O, —NH—$(C_1-C_4)$-alkyl, —NH—$((C_1-C_4)$-alkyl$)_2$, —$(C_1-C_8)$-alkyl, —$(C_1-C_8)$-alkoxy, halogen, nitro, amino, trifluoromethyl, hydroxyl, —$CF_3$, hydroxy-$(C_1-C_4)$-alkyl such as hydroxymethyl or 1-hydroxyethyl or 2-hydroxyethyl, methylenedioxy, ethylenedioxy, formyl, acetyl, cyano, hydroxycarbonyl, aminocarbonyl, —$(C_1-C_4)$-alkoxycarbonyl, phenyl, phenoxy, benzyl, benzyloxy, —$S(O)_x—R^{11}$, in which x is the integer zero, 1 or 2, —O—$(C_1-C_4)$-alkyl, —C(O)—OH, —C(O)—O—$(C_1-C_4)$-alkyl, —NH—C(O)—$(C_1-C_4)$-alkyl or tetrazolyl, or
2. heteroaryl having from 5 to 14 ring members, in which heteroaryl is defined as above and in which heteroaryl is unsubstituted or substituted, once, twice or three times, by identical or different radicals from the series —C(O)—$(C_1-C_4)$-alkyl, —C(O), =O, —NH—$(C_1-C_4)$-alkyl, —NH—$((C_1-C_4)$-alkyl$)_2$, —$(C_1-C_8)$-alkyl, —$(C_1-C_8)$-alkoxy, halogen, nitro, amino, trifluoromethyl, hydroxyl, —$CF_3$, hydroxy-$(C_1-C_4)$-alkyl such as hydroxymethyl or 1-hydroxyethyl or 2-hydroxyethyl, methylenedioxy, ethylenedioxy, formyl, acetyl, cyano, hydroxycarbonyl, aminocarbonyl, —$(C_1-C_4)$-alkoxycarbonyl, phenyl, phenoxy, benzyl, benzyloxy, —$S(O)_x$—$R^{11}$, in which x is the integer zero, 1 or 2, —O—$(C_1-C_4)$-alkyl, —C(O)—OH, —C(O)—O—$(C_1-C_4)$-alkyl, —NH—C(O)—$(C_1-C_4)$-alkyl or tetrazolyl.
The invention furthermore relates to the use, according to the invention, of the compound of the formula I, where
E is N atom or the radical —$C(R^{19})$—,
in which $R^{19}$ is hydrogen atom, one of the substituents $R^1$, $R^2$, $R^3$ and $R^4$ is a radical of the formula II, in which
$R^8$ is hydrogen atom,
$R^9$ is 1. a characteristic radical of an amino acid from the group histidine, serine, tryptophan, threonine, cysteine, methionine, asparagine, glutamine, lysine, arginine, glutamic acid and aspartic acid, or
2. —$(C_1-C_6)$-alkyl, in which alkyl is straight-chain or branched and is unsubstituted or substituted, once or twice, by
a) phenyl,
b) a radical from the group azepine, azetidine, benzimidazole, benzothiazole, benzothiophene, benzoxazole, diazepine, imidazole, indole, isothiazole, isoxazole, morpholine, 1,3,4-oxadiazole, 5-oxo4,5-dihydro-[1,3,4]oxadiazole, oxazole piperidine, pyrazine, pyrazole, pyridine, pyrimidine, pyrrole, pyrrolidine, pyrroline, thiazole, thiomorpholine, thiophene or triazole,
c) —$NH(R^{11})$,
d) —C(O)—$R^{12}$, in which
$R^{12}$ is naphthyl, phenyl, morpholinyl or pyrimidinyl,
e) —O—$R^{11}$,
f) —$N(R^{12})$-phenyl, in which $R^{12}$ is defined as above, g) —S(O)$_x$—R$^{12}$, in which x is zero, 1 or 2, and h) —CN, or i) —(C$_3$-C$_6$)-cycloalkyl, and the radicals defined above by a), b), d) and i) and R$^{12}$ are unsubstituted or are substituted, once or twice, by —OH, —(C$_1$-C$_4$)-alkyl, —CF$_3$, halogen, —O—(C$_1$-C$_4$)-alkyl, —COOH, —C(O)—O—(C$_1$-C$_4$)-alkyl, —NH$_2$ or —NH—C(O)—(C$_1$-C$_4$)-alkyl, Z is 1. a heteroaryl radical from the group 3-hydroxypyrro-2,4-dione, imidazole, imidazolidine, imidazoline, indazole, isothiazole, isothiazolidine, isoxazole, isoxazolidine, 2-isoxazolidine, isoxazolone, morpholine, 1,3,4-oxadiazole, oxadiazolidinedione, oxadiazolone, 1,2,3,5-oxathiadiazole-2-oxide, oxazole, 5-oxo-4,5-dihydro-[1,3,4]oxadiazole, 5-oxo-1,2,4-thiadiazole, piperazine, pyrazine, pyrazole, pyrazolidine, pyrazoline, pyridazine, pyrimidine, tetrazole, thiadiazole, thiazole, thiomorpholine, triazole or triazolone, and the heteroaryl radical is unsubstituted or substituted, once, twice or three times, independently of each other, by 1.1 —C(O)—R$^{15}$, in which R$^{15}$ is hydrogen atom or —(C$_1$-C$_4$)-alkyl, 1.2 —(C$_1$-C$_4$)-alkyl, 1.3 —O—R$^{15}$, in which R$^{15}$ is hydrogen atom or —(C$_1$-C$_4$)-alkyl, 1.4 —N(R$^{15}$)—R$^{16}$, in which R$^{15}$ and R$^{16}$ are, independently of each other, hydrogen atom or —(C$_1$-C$_4$)-alkyl, 1.5 halogen, or 1.6 keto radical, 2. —C(O)—R$^{15}$, in which R$^{15}$ is hydrogen atom or —(C$_1$-C$_4$)-alkyl, 3. —C(O)—R$^{15}$, in which R$^{15}$ is hydrogen atom or —(C$_1$-C$_4$)-alkyl, or 4. —C(O)—N(R$^{15}$)—R$^{16}$, in which R$^{15}$ and R$^{16}$ are, independently of each other, hydrogen atom or —(C$_1$-C$_4$)-alkyl, R$^{11}$ is 1. —(C$_1$-C$_4$)-alkyl, 2. R$^{13}$or, 3. —N(R$^{13}$)$_2$, in which R$^{13}$ is, independently of each other, a) hydrogen atom, b) —(C$_1$-C$_6$)-alkyl, c) —(C$_1$-C$_4$)-alkyl-O—(C$_1$-C$_4$)-alkyl, d) —(C$_1$-C$_6$)-alkyl-N(R$^{15}$)$_2$, in which R$^{15}$ is defined as above, or e) —(C0—C$_4$)-alkyl which is substituted, once or twice, by imidazolyl, morpholinyl or phenyl, or R$^8$ and R$^9$ form, together with the nitrogen atom and carbon atom to which they are in each case bonded, a ring of the formula IIa from the group pyrrole, pyrroline, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, isoxazole, 2-isoxazolidine, isoxazolidine, morpholine, isothiazole, thiazole, tetrazole, 1,2,3,5-oxathiadiazole-2-oxides, oxadiazolone, isoxazolone, triazolones, oxadiazolidinedione, triazole, which are substituted by F, CN, CF$_3$ or COO—(C$_1$-C$_4$)-alkyl, 3-hydroxypyrro-2,4-diones, 5-oxo-1,2,4-thiadiazoles, 1,3,4-oxadiazole, isothiazolidine, thiomorpholine, indazole, thiadiazole, benzimidazole, quinoline, triazole, phthalazine, quinazoline, quinoxaline, purine, pteridine, indole, tetrahydroquinoline, tetrahydroisoquinoline and isoquinoline, or R$^9$ and Z form, together with the carbon atoms to which they are in each case bonded, a ring of the formula IIc from the group pyrrole, pyrroline, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, isoxazole, 2-isoxazolidine, isoxazolidine, morpholine, isothiazole, thiazole, isothiazolidine, thiomorpholine, indazole, thiadiazole, benzimidazole, quinoline, triazole, phthalazine, quinazoline, quinoxaline, purine, pteridine, indole, tetrahydroquinoline, tetrahydroisoquinoline, isoquinoline, tetrazole, 1,2,3,5-oxathiadiazole-2-oxides, oxadiazolone, isoxazolone, triazolones, oxadiazolidinedione, triazole, which are substituted by F, CN, CF$_3$ or COO—(C$_1$-C$_4$)-alkyl, 3-hydroxypyrro-2,4-diones, 1,3,4-oxadiazole and 5-oxo-1,2,4-thiadiazole and the other substituents R$^1$, R$^2$, R$^3$ and R$^4$ in each case are, independently of each other, 1. hydrogen atom, 2. halogen, 3. —(C$_1$-C$_4$)-alkyl,

4. —CN,

5. —NO$_2$,

6. —O—(C$_0$-C$_4$)-alkyl-phenyl,

7. —O—(C$_1$-C$_4$)-alkyl,

8. —N—(C$_0$-C$_4$)-alkyl-phenyl,

9. —N—(C$_1$-C$_4$)-alkyl or

10. —CF$_3$,

R$^5$ is 1. hydrogen atom,

2. —OH, or

3. =O, and

R$^6$ is 1. phenyl, substituted, once or twice, by 1.1 —CN, 1.2 —NO$_2$, 1.3 —O—(C$_1$-C$_4$)-alkyl, or 1.4 —NH$_2$, or 2. is pyridine or pyrimidine, where pyridine or pyrimidine is unsubstituted or substituted, once, twice or three times, by identical or different radicals from the series —C(O)—(C$_1$-C$_4$)-alkyl, —C(O), =O, —NH—(C$^1$-C$_4$)-alkyl, —NH—((C$_1$-C$_4$)-alkyl)$_2$, —(C$_1$-C$_8$)-alkyl, —(C$_1$-C$_8$)-alkoxy, halogen, nitro, amino, trifluoromethyl, hydroxyl, —CF$_3$, hydroxy-(C$_1$-C$_4$)-alkyl such as hydroxymethyl or 1-hydroxyethyl or 2-hydroxyethyl, methylenedioxy, ethylenedioxy, formyl, acetyl, cyano, hydroxycarbonyl, aminocarbonyl, —(C$_1$-C$_4$)-alkoxycarbonyl, phenyl, phenoxy, benzyl, benzyloxy, —S(O)$_x$—R$^{11}$, in which x is the integer zero, 1 or 2, —O—(C$_1$-C$_4$)-alkyl, —C(O)—OH, —C(O)—O—(C$_1$-C$_4$)-alkyl, —NH—C(O)—(C$_1$-C$_4$)-alkyl or tetrazolyl.

The invention furthermore relates to the use, according to the invention, of the compound of the formula I, where E is the radical —C(R$^{19}$)—, in which R$^{19}$ is hydrogen atom or R$^9$, one of the substituents R$^1$, R, R$^3$ and R$^4$ is a radical of the formula II in which D is —C(O)—, R$^8$ is hydrogen atom, Z is 5-oxo4,5-dihydro-[1,3,4]oxadiazole, —C(O)—OH or —C(O)—NH$_2$, R$^9$ is 1. —(C$_1$-C$_4$)-alkyl, in which alkyl is straight-chain or branched and is substituted once or twice, independently of each other, by 1.1 —S(O)—R$^{11}$, where R$^{11}$ is defined as below, 1.2 —N(R$^{11}$)$_2$, where R$^{11}$ is defined as below, or 1.3 pyrrole, or 2. the characteristic radical of an amino acid from the group histidine, tryptophan, serine, threonine, cysteine, methionine, asparagine, glutamine, lysine, arginine, glutamic acid and aspartic acid, $R^{11}$ is a) hydrogen atom,
b) —($C_1$-$C_6$)-alkyl, in which alkyl is unsubstituted or substituted, once or three times, independently of each other, by halogen, or
c) phenyl, in which phenyl is unsubstituted or substituted, once to three times, independently of each other, by halogen or —($C_1$-$C_4$)-alkyl, the other substituents $R^1$, $R^2$, $R^3$ and $R^4$ are in each case hydrogen atom,
$R^5$ is hydrogen atom, and
$R^6$ is phenyl, pyridine or pyrimidine,
where phenyl, pyridine or pyrimidine is unsubstituted or substituted, once, twice or three times, by identical or different radicals from the series —C(O)—($C_1$-$C_4$)-alkyl, —C(O), =O, —NH—($C_1$-$C_4$)-alkyl, —NH—(($C_1$-$C_4$)-alkyl)$_2$, —($C_1$-$C_8$)-alkyl, —($C_1$-$C_8$)-alkoxy, halogen, nitro, amino, trifluoromethyl, hydroxyl, —$CF_3$, hydroxy-($C_1$-$C_4$)-alkyl such as hydroxymethyl or 1-hydroxyethyl or 2-hydroxyethyl, methylenedioxy, ethylenedioxy, formyl, acetyl, cyano, hydroxycarbonyl, aminocarbonyl, —($C_1$-$C_4$)-alkoxycarbonyl, phenyl, phenoxy, benzyl, benzyloxy, —S(O)$_x$—$R^{11}$, in which x is the integer zero, 1 or 2, —O—($C_1$-$C_4$)-alkyl, —C(O)—OH, —C(O)—O—($C_1$-$C_4$)-alkyl, —NH—C(O)—($C_1$-$C_4$)-alkyl or tetrazolyl.

The invention furthermore relates to the use, according to the invention, of the compound of the formula Ia

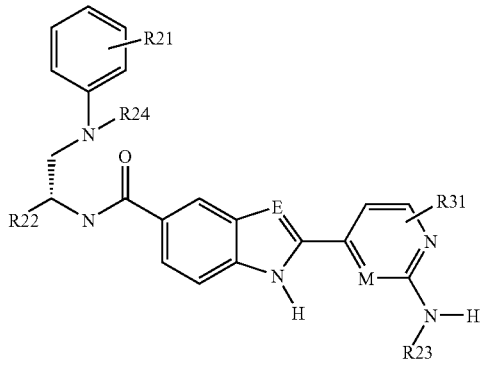

(Ia)

and/or a stereoisomeric form of the compound of the formula Ia and/or a physiologically tolerated salt of the compound of the formula Ia, where
E and M are identical or different and are, independently of each other N atom or CH
R21 and R31 are identical or different and are, independently of each other,
1. hydrogen atom,
2. halogen,
3. —($C_1$-$C_4$)-alkyl,
4. —CN,
5. —$CF_3$,
6. —$OR^{15}$, in which $R^{15}$ is hydrogen atom or —($C_1$-$C_4$)-alkyl,
7. —N($R^{15}$)—$R^{16}$, in which $R^{15}$ and $R^{16}$ are, independently of each other, hydrogen atom or —($C_1$-$C_4$)-alkyl,
8. —C(O)—$R^{15}$, in which $R^{15}$ is hydrogen atom or $C_1$-$C_4$-alkyl, or
9. —S(O)$_x$—$R^{15}$ in which x is the integer zero, 1 or 2, and $R^{15}$ is hydrogen atom or —($C_1$-$C_4$)-alkyl, R22 is 1. a heteroaryl radical from the group 3-hydroxypyrro-2,4-dione, imidazole, imidazolidine, imidazoline, indazole, isothiazole, isothiazolidine, isoxazole, 2-isoxazolidine, isoxazolidine, isoxazolone, morpholine, oxazole, 1,3,4-oxadiazole, oxadiazolidinedione, oxadiazolone, 1,2,3,5-oxathiadiazole-2-oxide, 5-oxo-4,5-dihydro-[1,3,4]oxadiazole, 5-oxo-1,2,4-thiadiazole, piperazine, pyrazine, pyrazole, pyrazoline, pyrazolidine, pyridazine, pyrimidine, tetrazole, thiadiazole, thiazole, thiomorpholine, triazole or triazolone, and
the heteroaryl radical is unsubstituted or is substituted once, twice or three times, independently of each other, by
1.1 —C(O)—$R^{15}$, in which $R^{15}$ is hydrogen atom or —($C_1$-$C_4$)-alkyl,
1.2 —($C_1$-$C_4$)-alkyl,
1.3 —O—$R^{15}$, in which $R^{15}$ is hydrogen atom or $C_1$-$C_4$-alkyl,
1.7 —N($R^{15}$)—$R^{16}$, in which $R^{15}$ and $R^{16}$ are, independently of each other, hydrogen atom or —($C_1$-$C_4$)-alkyl,
1.8 halogen, or
1.9 keto radical,
2. —C(O)—$R^{15}$, in which $R^{15}$ is hydrogen atom or —($C_1$-$C_4$)-alkyl,
3. —C(O)—$OR^{15}$, in which $R^{15}$ is hydrogen atom or —($C_1$-$C_4$)-alkyl, or
4. —C(O)—N($R^{17}$)—$R^{18}$, in which $R^{17}$ and $R^{18}$ are, independently of each other, hydrogen atom, —($C_1$-$C_4$)-alkyl-OH, —O—($C_1$-$C_4$)-alkyl or —($C_1$-$C_4$)-alkyl,
$R^{23}$ is hydrogen atom or —($C_1$-$C_4$)-alkyl,
$R^{24}$ is 1. a heteroaryl radical from the group pyrrole, furan, thiophene, imidazole, pyrazole, oxazole, isoxazole, thiazole, isothiazole, tetrazole, 1,2,3,5-oxathiadiazole-2-oxides, triazolones, oxadiazolones, isoxazolones, oxadiazolidinediones, triazoles, 3-hydroxypyrro-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline, β-carboline and benzo fused cyclopenta derivatives or cyclohexa derivatives of these heteroaryl radicals,
where the heteroaryl radical is unsubstituted or is substituted, once, twice or three times, independently of each other, by —($C_1$-$C_5$)-alkyl, —($C_1$-$C_5$)-alkoxy, halogen, nitro, amino, trifluoromethyl, hydroxyl, hydroxy-($C_1$-$C_4$)-alkyl, methylenedioxy, ethylenedioxy, formyl, acetyl, cyano, hydroxycarbonyl, aminocarbonyl or —($C_1$-$C_4$)-alkoxycarbonyl, or
2. an aryl radical from the group phenyl, naphthyl, 1-naphthyl, 2-naphthyl, biphenylyl, 2-biphenylyl, 3-biphenylyl and 4-biphenylyl, anthryl or fluorenyl, and the aryl radical is unsubstituted or substituted, once, twice or three times, independently of each other, by —($C_1$-$C_5$)-alkyl, —($C_1$-$C_5$)-alkoxy, halogen, nitro, amino, trifluoromethyl, hydroxyl, hydroxy-($C_1$-$C_4$)-alkyl, methylenedioxy, ethylenedioxy, formyl, acetyl, cyano, hydroxycarbonyl, aminocarbonyl or —($C_1$-$C_4$)-alkoxycarbonyl.

The invention furthermore relates to the use, according to the invention, of the compound of the formula Ia, where
E and M are identical or different and are, independently of each other, N atom or CH,
R21 and R31 are identical or different and, independently of each other, are defined as above under 1. to 9.,
R22 is 1. a heteroaryl radical from the group imidazole, isothiazole, isoxazole, 2-isoxazolidine, isoxazolone, 1,3,4-oxadiazole, oxadiazolidinedione, 1,2,3,5-oxadiazole, oxazole, 5-oxo4,5-dihydro-[1,3,4]oxadiazole, tetrazole, thiadiazole, thiazole, triazole or triazolone, and the heteroaryl radical is unsubstituted or is substituted once, twice or three times, independently of each other, by
1.1 keto radical,
1.2 halogen or
1.3 —($C_1$-$C_2$)-alkyl, or
2. —C(O)—N($R^{17}$)—$R^{18}$, in which $R^{17}$ and $R^{18}$ are, independently of each other, hydrogen atom, —($C_1$-$C_4$)-alkyl-OH, —O—($C_1$-$C_4$)-alkyl, or —($C_1$-$C_4$)-alkyl, $R^{23}$ is hydrogen atom, methyl or ethyl, $R^{24}$ is 1. a heteroaryl radical from the group of the unsaturated, partially saturated or completely saturated rings which are derived from pyridine, pyrazine, pyrimidine, pyridazine, pyrrole, furan, thiophene, imidazole, pyrazole, oxazole, isoxazole, thiazole, triazole or isothiazole, where the heteroaryl radical is unsubstituted or substituted, once, twice or three times, independently of each other, by —($C_1$-$C_4$)-alkyl, —($C_1$-$C_4$)-alkoxy, F, Cl, I, Br, nitro, amino, trifluoromethyl, hydroxyl, hydroxy-($C_1$-$C_4$)-alkyl, methylenedioxy, ethylenedioxy, formyl, acetyl, cyano, hydroxycarbonyl, aminocarbonyl or —($C_1$-$C_4$)-alkoxycarbonyl, or 2. phenyl and phenyl is unsubstituted or is substituted once, twice or three times, independently of each other, by F, Cl, I, Br, $CF_3$, —OH, —($C_1$-$C_4$)-alkyl or —($C_1$-$C_4$)-alkoxy.

The invention furthermore relates to the use, according to the invention, of the compound N-[(S)-2-diphenylamino-1-(5-oxo4,5-dihydro-[1,3,4]oxadiazol-2-yl)ethyl]-2-(2-methylaminopyrimidin-4-yl)-1H-indole-5-carboxamide or N-((S)-1-carbamoyl-2-diphenylaminoethyl)-2-(2-methylaminopyrimidin-4-yl)-1H-benzimidazole-5-carboxamide.

Definition of Terms

As used above, and throughout the description of the invention, the following terms, unless otherwise indicated, shall be understood to have the following meanings.

"Patient" includes both human and other mammals.

"Pharmaceutically effective amount" is meant to describe an amount of a compound, composition, medicament or other active ingredient effective in producing the desired therapeutic effect.

"Optionally substituted" means either unsubstituted or substituted one or more times by substituents, which may be the same, or different.

The term "halogen" is understood as meaning fluorine, chlorine, bromine or iodine. The terms "—($C_1$-$C_8$)-alkyl", "—($C_1$-$C_6$)-alkyl" and "—($C_1$-$C_4$)-alkyl" are understood as meaning hydrocarbon radicals whose carbon chain is straight-chain or branched and contains from 1 to 8, from 1 to 6 and from 1 to 4 carbon atoms, respectively, such as methyl, ethyl, propyl, butyl, tert-butyl, pentyl, hexyl, heptyl or octyl. The term "—($C_0$)-alkyl" is understood as meaning a covalent bond. Examples of cyclic alkyl radicals are 3- to 6-membered monocycles such as cyclopropyl, cyclobutyl, cyclopentyl and cyclohexyl.

The phrase "$R^8$ and $R^9$ form, together with the nitrogen atom and carbon atom to which they are in each case bonded, a heterocyclic ring of the formula II$a$" is understood as meaning radicals which are derived from pyrrole, pyrroline, pyrrolidine, imidazole, pyrazole, oxazole, isoxazole, tetrazole, isoxazoline, isoxazolidine, morpholine, thiazole, isothiazole, isothiazoline, purine, isothiazolidine, thiomorpholine, pyridine, piperidine, pyrazine, piperazine, pyrimidine, pyridazine, indole, isoindole, indazole, benzimidazole, phthalazine, quinoline, isoquinoline, quinoxaline, quinazoline, cinnoline, pteridine, triazolones, tetrazole, 1,2,3,5-oxathiadiazole-2-oxides, oxadiazolones, isoxazolones, oxadiazolidinediones, triazoles, which are substituted by F, —CN, —$CF_3$ or —C(O)—O—($C_1$-$C_4$)-alkyl, 3-hydroxypyrro-2,4-diones, 5-oxo-1,2,4-thiadiazoles, imidazolidine, carboline and benzofused derivatives of these heterocycles.

The phrase "$R^9$ and Z form, together with the carbon atoms to which they are in each case bonded, a heterocyclic ring of the formula II$c$ " is understood as meaning radicals which [lacuna] from the group pyrrole, pyrroline, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, isoxazole, 2-isoxazolidine, isoxazolidine, morpholine, isothiazole, thiazole, isothiazolidine, thiomorpholine, indazole, thiadiazole, benzimidazole, quinoline, triazole, phthalazine, quinazoline, quinoxaline, purine, pteridine, indole, tetrahydroquinoline, tetrahydroisoquinoline, isoquinoline, tetrazole, 1,2,3,5-oxathiadiazole-2-oxides, oxadiazolone, isoxazolone, triazolone, 3-hydroxypyrro-2,4-diones, 1,3,4-oxadiazole and 5-oxo-1,2,4-thiadiazole, oxadiazolidinedione, triazole, which are unsubstituted or substituted by F, CN, $CF_3$ or C(O)—O—($C_1$-$C_4$)-alkyl.

The phrase "heteroaryl radical from the group of the unsaturated, partially saturated or completely saturated rings which are derived from pyridine, pyrazine, pyrimidine, pyridazine, pyrrole, furan, thiophene, imidazole, pyrazole, oxazole, isoxazole, thiazole and isothiazole", is understood as meaning, for example, compounds such as piperazine, pyrazoline, imidazoline, pyrazolidine, imidazolidine, tetrahydropyridine, isoxazoline, isoxazolidine, morpholine, isothiazoline, isothiazolidine, tetrahydro-1,4-thiazine and piperidine.

The term "aryl" is understood as meaning aromatic hydrocarbon radicals having from 6 to 14 carbon atoms in the ring. Examples of —($C_6$-$C_{14}$)-aryl radicals are phenyl, naphthyl, for example 1-naphthyl and 2-naphthyl, biphenylyl, for example 2-biphenylyl, 3-biphenylyl and 4-biphenylyl, anthryl and fluorenyl. Biphenylyl radicals, naphthyl radicals and, in particular, phenyl radicals are preferred aryl radicals. Aryl radicals, in particular phenyl radicals, can be substituted once or more than once, preferably once, twice or three times, by identical or different radicals, preferably by radicals from the series —($C_1$-$C_8$)-alkyl, in particular —($C_1$-$C_4$)-alkyl, —($C_1$-$C_8$)-alkoxy, in particular —($C_1$-$C_4$)-alkoxy, halogen, nitro, amino, trifluoromethyl, hydroxyl, hydroxy-($C_1$-$C_4$)-alkyl, such as hydroxymethyl or 1-hydroxyethyl or 2-hydroxyethyl, methylenedioxy, ethylenedioxy, formyl, acetyl, cyano, hydroxycarbonyl, aminocarbonyl, —($C_1$-$C_4$)-alkoxycarbonyl, phenyl, phenoxy, benzyl, benzyloxy and tetrazolyl. The same applies, in a corresponding manner, for example, for radicals such as arylalkyl or arylcarbonyl. Arylalkyl radicals are, in particular, benzyl and also 1- and 2-naphthylmethyl, 2-, 3- and 4-biphenylylmethyl and 9-fluorenylmethyl. Substituted arylalkyl radicals are, for example, benzyl radicals and naphthylmethyl radicals which are substituted, in the aryl moiety, by one or more —($C_1$-$C_8$)-alkyl radicals, in particular —($C_1$-$C_4$)-alkyl radicals, for example 2-, 3- and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7- and 8-methyl-1-naphthylmethyl, and 1-, 3-, 4-, 5-, 6-, 7- and 8-methyl-2-naphthylmethyl, benzyl radicals and naphthylmethyl radicals which are substituted, in the aryl moiety, by one or more —($C_1$-$C_8$)-alkoxy radicals, in particular —($C_1$-$C_4$)-alkoxy radicals, for example 4-methoxybenzyl, 4-neopentyloxybenzyl, 3,5-dimethoxybenzyl, 3,4-methylenedioxybenzyl and 2,3,4-trimethoxybenzyl, nitrobenzyl radicals, for example 2-, 3- and 4-nitrobenzyl, halobenzyl radicals, for example 2-, 3- and 4-chlorobenzyl, 2-, 3- and 4-fluorobenzyl, 3,4-dichlorobenzyl, pentafluorobenzyl and trifluoromethylbenzyl radicals, for example 3- and 4-trifluoromethylbenzyl and 3,5-bis(trifluoromethyl)benzyl.

In monosubstituted phenyl radicals, the substituent can be located in the 2 position, the 3 position or the 4 position. Doubly substituted phenyl can be substituted in the 2,3 position, the 2,4 position, the 2,5 position, the 2,6 position, the 3,4 position or the 3,5 position. In triply substituted phenyl radicals, the substituents can be located in the 2,3,4 position, the 2,3,5 position, the 2,4,5 position, the 2,4,6 position, the 2,3,6 position or the 3,4,5 position.

The comments made with regard to the aryl radicals apply, in a corresponding manner, to divalent arylene radicals, for example to phenylene radicals, which can be present, for example, as 1,4-phenylene or as 1,3-phenylene. Phenylene-$(C_1$-$C_6)$-alkyl is, in particular, phenylenemethyl ($-C_6H_4-CH_2-$) and phenyleneethyl, $(C_1$-$C_6)$-alkylenephenyl, in particular methylenephenyl ($-CH_2-C_6H_4-$). Phenylene-$(C_2$-$C_6)$-alkenyl is, in particular, phenyleneethenyl and phenylenepropenyl.

The phrase "heteroaryl having from 5 to 14 ring members" means a radical of a monocyclic or polycyclic aromatic system having from 5 to 14 ring members which contains 1, 2, 3, 4 or 5 heteroatoms as ring members. Examples of heteroatoms are N, O and S. If several heteroatoms are present, they may be identical or different. Heteroaryl radicals can also be substituted, once or more than once, preferably once, twice or three times, by identical or different radicals from the series $-(C_1$-$C_8)$-alkyl, in particular $-(C_1$-$C_4)$-alkyl, $-(C_1$-$C_8)$-alkoxy, in particular $-(C_1$-$C_4)$-alkoxy, halogen, nitro, $-N(R^{10})_2$, trifluoromethyl, hydroxyl, hydroxy-$(C_1$-$C_4)$-alkyl, such as hydroxymethyl or 1-hydroxyethyl or 2-hydroxyethyl, methylenedioxy, formyl, acetyl, cyano, hydroxycarbonyl, aminocarbonyl, $-(C_1$-$C_4)$-alkoxycarbonyl, phenyl, phenoxy, benzyl, benzyloxy and tetrazolyl. Heteroaryl having from 5 to 14 ring members is preferably a monocyclic or bicyclic aromatic radical which contains 1, 2, 3 or 4, in particular 1, 2 or 3, identical or different heteroatoms from the series N, O and S, and which can be substituted by 1, 2, 3 or 4, in particular 1 to 3, identical or different substituents from the series $-(C_1$-$C_6)$-alkyl, $-(C_1$-$C_6)$-alkoxy, fluorine, chlorine, nitro, $-N(R^{10})_2$, trifluoromethyl, hydroxyl, hydroxy-$(C_1$-$C_4)$-alkyl, $-(C_1$-$C_4)$-alkoxycarbonyl, phenyl, phenoxy, benzyloxy and benzyl. Particularly preferably, heteroaryl is a monocyclic or bicyclic aromatic radical having from 5 to 10 ring members, in particular a 5-membered to 6-membered monocyclic aromatic radical which contains 1, 2 or 3, in particular 1 or 2, identical or different heteroatoms from the series N, O and S and which can be substituted by 1 or 2 identical or different substituents from the series $-(C_1$-$C_4)$-alkyl, halogen, hydroxyl, $-N(R^1)_2$, $-(C_1$-$C_4)$-alkoxy, phenyl, phenoxy, benzyloxy and benzyl.

The term "heterocycle having from 5 to 12 ring members" means a monocyclic or bicyclic 5-membered to 12-membered heterocyclic ring which is partially saturated or completely saturated. Examples of heteroatoms are N, O and S. The heterocycle is unsubstituted or is substituted by identical or different substituents at one or more carbon atoms or at one or more heteroatoms. These substituents have been defined above in connection with the heteroaryl radical. In particular, the heterocyclic ring is substituted at carbon atoms, once or more than once, for example once, twice, three times or four times, by identical or different radicals from the series $-(C_1$-$C_8)$-alkyl, for example $-(C_1$-$C_4)$-alkyl, $-(C_1$-$C_8)$-alkoxy, for example $-(C_1$-$C_4)$-alkoxy, such as methoxy, phenyl-$(C_1$-$C_4)$-alkoxy, for example benzyloxy, hydroxyl, oxo, halogen, nitro, amino or trifluoromethyl and/or is substituted at the ring nitrogen atom(s) in the heterocyclic ring by $-(C_1$-$C_8)$-alkyl, for example $-(C_1$-$C_4)$-alkyl such as methyl or ethyl, by optionally substituted phenyl or phenyl-$(C_1$-$C_4)$-alkyl, for example benzyl. Nitrogen heterocycles can also be present as N-oxides or as quaternary salts.

Examples of the terms heteroaryl having from 5 to 14 ring members and heterocycle having from 5 to 12 ring members are radicals which are derived from pyrrole, furan, thiophene, imidazole, pyrazole, oxazole, isoxazole, thiazole, isothiazole, tetrazole, 1,2,3,5-oxathiadiazole-2-oxides, triazolones, oxadiazolones, isoxazolone, oxadiazolidinedione, triazole, which are substituted by F, $-CN$, $-CF_3$ or $-C(O)-O-(C_1$-$C_4)$-alkyl, 3-hydroxypyrro-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline, -carboline and benzo fused, cyclopenta fused, cyclohexa fused or cyclohepta fused derivatives of these heterocycles. Particular preference is given to the radicals 2- or 3-pyrrolyl, phenylpyrrolyl, such as 4- or 5-phenyl-2-pyrrolyl, 2-furyl, 2-thienyl, 4-imidazolyl, methylimidazolyl, for example 1-methyl-2-, -4- or -5-imidazolyl, 1,3-thiazol-2-yl, 2-pyridyl, 3-pyridyl, 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolinyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl or dihydropyridinyl, pyrrolidinyl, for example 2- or 3-(N-methylpyrrolidinyl), piperazinyl, morpholinyl, thiomorpholinyl, tetrahydrothienyl and benzodioxolanyl.

DETAILED DESCRIPTION OF THE INVENTION

The general structural formula of α-amino acids is as follows:

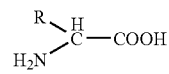

The α-amino acids differ from each other in the radical R which, within the context of the present application, is designated the "characteristic radical" of an amino acid. When $R^9$ denotes the characteristic radical of amino acid, use is preferably made of the characteristic radicals of the following naturally occurring α-amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid. Particular preference is given to histidine, tryptophan, serine, threonine, cysteine, methionine, asparagine, glutamine, lysine, arginine, glutamic acid and aspartic acid. In addition, amino acids which do not occur naturally, such as 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydroisoquinoline-3-carboxylic acid, 2-aminopimellic acid, phenylglycine, 3-(2-thienyl)alanine, 3-(3-thienyl)alanine, 2-(2-thienyl)glycine, 2-aminoheptanoic acid, pipecolic acid, hydroxylysine, sarcosine, N-methylisoleucine, 6-N-methyllysine, N-methylvaline, norvaline, norleucine, ornithine, alloisoleucine, allothreonine, allohydroxylysine, 4-hydroxyproline, 3-hydroxyproline, 3-(2-naphthyl)alanine, 3-(1-naphthylalanine), homophenylalanine, homocysteine, homocysteic acid, homotryptophan, cysteic acid, 3-(2-pyridyl)alanine, 3-(3-pyridyl)alanine, 3-(4-pyridyl)alanine, 2-amino-3-phenylaminopropionic acid, 2-amino-3-phenylaminoethylpropionic acid, phosphinothricin, 4-fluorophenylalanine, 3-fluorophenyl-alanine, 4-fluorophenylalanine, 3-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide or —NH—NR$^{11}$—C(O)N(R$^{11}$)$_2$, which are also substituted, where appropriate, are also preferred characteristic radicals of amino acid which are employed as the radical R$^8$. When amino acids which occur naturally, and also amino acids which do not occur naturally, possess a functional group such as amino, hydroxyl, carboxyl, mercapto, guanidyl, imidazolyl or indolyl, this group can also be protected.

The N-protecting groups which are customary in peptide chemistry, for example protecting groups of the urethane type, benzyloxycarbonyl (Z), t-butyloxycarbonyl (Boc), 9-fluorenyloxycarbonyl (Fmoc), allyloxycarbonyl (Aloc), or of the acid amide type, in particular formyl, acetyl or trifluoroacetyl, and also of the alkyl type, for example benzyl, are preferably used as suitable protecting groups for this purpose. When an imidazole radical is present in R$^8$, the sulfonic acid derivative of the formula IV, which is employed for the sulfonamide formation, serves, for example, as the group for protecting the imidazole nitrogen, which group can be eliminated once again in the presence of bases such as sodium hydroxide.

The compounds of the formulae I, I$a$ and I$b$ are prepared as described in patent applications WO 01/00610 and WO 01/30774, the content of each of which is incorporated herein by reference. The starting compounds for the chemical reactions are known or can be readily prepared using methods known from the literature.

EMBODIMENTS

Due to the pharmacological properties, which are evident in the models employed, of the IκB-kinase inhibitors which are used in accordance with the invention, said inhibitors are suitable for being employed in all forms of pain, in particular in association with pains in which inflammatory processes play a role.

The pharmaceuticals according to the invention can be administered orally, by inhalation, rectally or transdermally or by means of subcutaneous, intraarticular, intraperitoneal or intravenous injection. Oral or intraarticular administration is preferred.

The invention also relates to a process for producing a pharmaceutical which comprises bringing at least one compound of the formulae I or Ia, together with a pharmaceutically suitable and physiologically tolerated excipient and, where appropriate, other suitable active compounds, additives or auxiliary substances, into a suitable form for administration.

Examples of suitable solid or galenic preparation forms are granules, powders, sugar-coated tablets, tablets, (micro)capsules, suppositories, syrups, juices, suspensions, emulsions, drops or injectable solutions, and also preparations with protracted active compound release, in the preparation of which customary auxiliary substances, such as carrier substances, disintegrants, binders, coating agents, swelling agents, glidants or lubricants, flavorings, sweeteners and solubilizers are used. Frequently employed auxiliary substances which may be mentioned are magnesium carbonate, titanium dioxide, lactose, mannitol and other sugars, talc, milk protein, gelatin, starch, cellulose and its derivatives, animal and vegetable oils, such as cod liver oil, sunflower oil, groundnut oil or sesame oil, polyethylene glycol and solvents, such as sterile water and monohydric or polyhydric alcohols, such as glycerol. The pharmaceutical preparations are preferably produced and administered in dosage units, with each unit containing as the active constituent a particular dose of the compound of the formula I according to the invention. In the case of solid dosage units, such as tablets, capsules, sugar-coated tablets or suppositories, this dose can be up to about 1000 mg, preferably from about 50 mg to 300 mg, and, in the case of injection solutions in ampoule form, up to about 300 mg, preferably from about 10 mg to 100 mg. Depending on the activity of the compound according to the formulae I or Ia, daily doses of from about 20 mg to 1000 mg of active compound, preferably of from about 100 mg to 500 mg, are indicated for treating an adult patient of about 70 kg in weight. However, higher or lower daily doses may also possibly be appropriate. The daily dose can be administered either by means of a once-only administration in the form of a single dosage unit, or of several smaller dosage units, or by means of the multiple administration of subdivided doses at predetermined intervals.

As a rule, mass-spectroscopic methods (FAB-MS, ESI-MS) are used for determining end products. Temperatures are given in degrees centigrade; RT denotes room temperature (from 22° C. to 26° C.). Abbreviations which are used are either explained or correspond to the customary conventions. The invention is explained in more detail below with the aid of examples.

EXAMPLES

Preparation Examples

A.1.) Synthesis of the Amino Acid (methyl (S)-2-amino-3-diphenylaminopropionate (5))

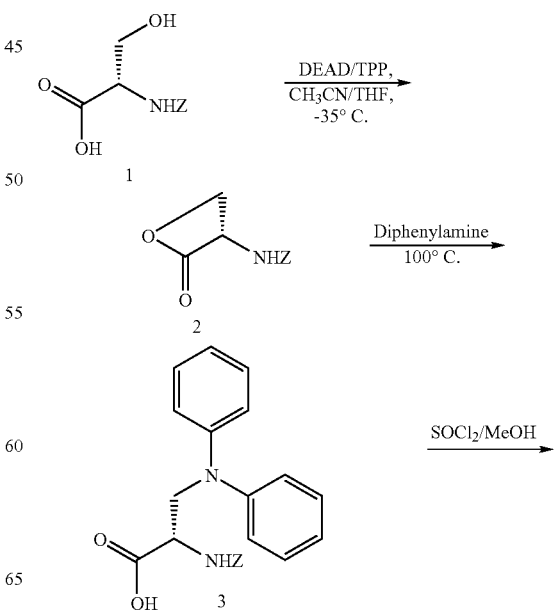

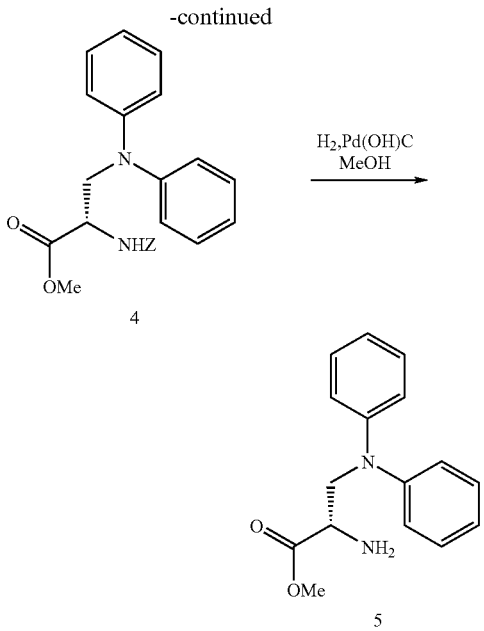

N-Benzyloxycarbonyl-L-serine-β-lactone (2)

54.8 g (0.209 mol) of triphenylphosphine were suspended in 600 ml of acetonitrile and the mixture was cooled down to −35° C. to −45° C. while excluding moisture. 36.4 g (0.209 mol) of diethyl azodicarboxylate were added dropwise at this temperature within the space of 50 minutes. The mixture was subsequently stirred at −35° C. for 15 minutes. A solution of 50 g (0.209 mol) of N-benzyloxycarbonyl-L-serine (1) in 500 ml of acetonitrile was then slowly added dropwise to this mixture such that the temperature did not rise above −35° C. The mixture was then stirred at 5° C. for 12 h. In order to terminate the reaction, the reaction solution was freed from the solvent under reduced pressure and the crude product was purified by means of medium-pressure chromatography on silica gel. (DCM/AcCN: 25/1). 20.8 g of N-benzyloxycarbonyl-L-serine-β-lactone (2) were obtained after the solvent had been removed; yield 45%; (see also Org. Synth. 1991 (70) 1 ff.) in fine needles.

Empirical formula $C_{11}H_{11}NO_4$; M.W.=221.2; MS (M+H) 222.1; $^1$H NMR (DMSO-$d_6$) 4.30 (m, 1H), 4.45 (m, 1H), 5.10 (s, 2H), 5.22 (m, 2H), 7.45 (m, 5H), 8.20 (d, J=9.8 Hz, 1H).

(S)-2-Benzyloxycarbonylamino-3-diphenylaminopropionic Acid (3)

5.0 g (22.6 mmol) of serine lactone (2) were mixed by stirring with 20 g (118.2 mmol) of diphenylamine, and the mixture was heated at 100° C. for 2 h. The crude product was purified by means of medium-pressure chromatography on silica gel. (DCM/methanol: 9/1, then EA/n-heptane: 4/1). 3.65 g (yield 42%) of pure 2-benzyloxycarbonylamino-3-diphenylaminopropionic acid (3) were obtained after the solvent had been removed.

Empirical formula $C_{23}H_{22}N_2O_4$; M.W.=390.44; MS (M+H) 391.2; $^1$H NMR (DMSO-$d_6$) 3.85 (m, 1H), 4.18 (m, 1H), 4.3 (m, 1H), 4.9 (m, 2H), 6.9 (m, 5H), 7.25 (m, 10H).

Methyl (S)-benzyloxycarbonylamino-3-diphenylaminopropionate (4)

6.5 ml (89.1 mmol) of thionyl chloride were added dropwise, at −5° C., to 75 ml of methanol and the mixture was stirred for 15 min. 3.6 g (9.22 mmol) of 2-benzyloxycarbonylamino-3-diphenylaminopropionic acid (3), dissolved in 75 ml of methanol, were then added and the mixture was stirred at room temperature for a further 3 hours (h). After the solvents had been evaporated, the residue was taken up in ethyl acetate and extracted with sodium carbonate solution. The purification by means of flash chromatography (n-heptane/ethyl acetate 7:3) yielded 2.76 g (50% yield) of methyl 2-benzyloxycarbonylamino-3-diphenylaminopropionate (4).

Empirical formula $C_{24}H_{24}N_2O_4$; M.W.=404.47; MS (M+H) 405.2; $^1$H NMR (DMSO-$d_6$) 3.58 (s, 3H), 3.95 (m, 1H), 4.18 (m, 1H), 4.4 (m, 1H), 4.95 (m, 2H), 6.9 (m, 6H), 7.3 (m, 9H), 7.85 (d, J=9.8 Hz, 1H).

Methyl (S)-2-amino-3-diphenylaminopropionate (5)

In order to eliminate the Z protecting group, 2.7 g (6.68 mmol) of the Z-protected derivative (4) were dissolved in 500 ml of methanol, and 100 mg of catalyst (10% Pd(OH)$_2$—C) were supplied under a protective atmosphere of nitrogen. The inert gas was subsequently displaced with a large excess of hydrogen and the mixture was shaken for 2 h in the hydrogen atmosphere. In order to terminate the reaction, the catalyst was filtered off and the filtrate was concentrated. 1.65 g (yield: 91%) of methyl 2-amino-3-diphenylaminopropionate (5) were obtained.

Empirical formula $C_{16}H_{18}N_2O_2$; M.W.=270.32; MS (M+H) 271.2; $^1$H NMR (DMSO-d6) 3.45 (s, 3H), 3.58 (m, 1H), 3.8 (m, 1H), 3.95 (m, 1H), 6.9 (m, 6H), 7.3 (m, 4H).

A.2.) Synthesis of the Heterocyclic Parent Substance (2-(2-methylaminopyrimidin-4-yl)-1H-indole-5-carboxylic Acid (10))

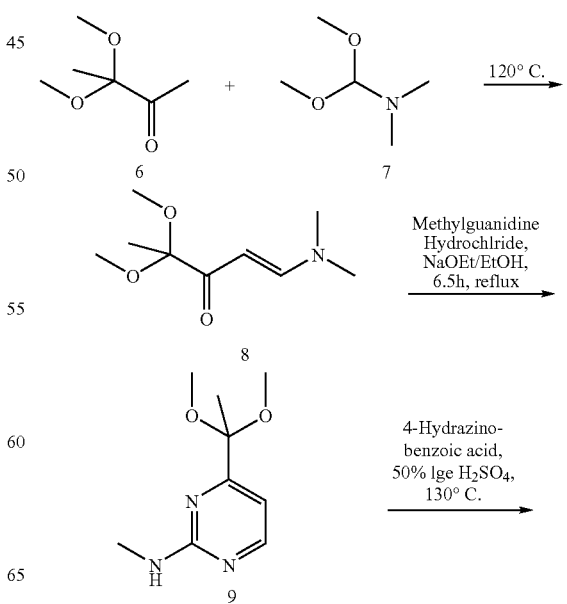

-continued

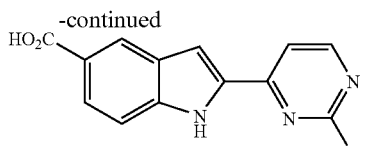

1-Dimethylamino-4,4-dimethoxypent-1-en-3-one (8)

100 g (0.76 mol) of 3,3-dimethoxy-2-butanone were stirred, at 120° C. for 48 h, with 90.2 g of N,N-dimethylformamide dimethylacetal (0.76 mol). The methanol which was formed during the reaction was continuously removed from the reaction solution by distillation. When the solution was cooled, spontaneous crystallization occurred, with this crystallization being brought to completion by adding a little heptane. This resulted in 128.24 g of crude product 8 (yield 90%), which was subjected to reaction without any further purification.

Empirical formula $C_9H_{17}NO_3$; M.W.=187.24; MS (M+H) 188.2; $^1$H NMR (DMSO-$d_6$) 1.22 (s, 3H), 2.80 (s, 3H), 3.10 (s, 9H), 5.39 (d, J=15 Hz, 1H), 7.59 (d, J=15 Hz, 1H).

[4-(1,1-Dimethoxyethyl)pyrimidin-2-yl]methylamine (9)

1.22 g (53 mmol) of sodium were dissolved in 100 ml of absolute ethanol. 5.8 g (53 mmol) of methylguanidine hydrochloride and 10 g (53 mmol) of 1-dimethylamino4,4-dimethoxypent-1-en-3-one (8) were added, with stirring, to this solution, which was heated at boiling heat for 4 h. In order to terminate the reaction, the ethanol was evaporated. The product 9, which was obtained in this way, was used for the subsequent reaction without any further purification. Yield 11.5 g (58 mmol, quantitative).

Empirical formula $C_9H_{15}N_3O_2$; M.W.=197.24; MS (M+H) 198.2; $^1$H NMR (DMSO-$d_6$) 1.45 (s, 3H), 2.78 (s, 3H), 3.10 (s, 6H), 6.75 (d, J=3 Hz, 1H), 7.0-7.1 (s(b), 1H), 8.30(d, J=3 Hz, 1H).

2-(2-Methylaminopyrimidin4-yl)-1H-indole-5-carboxylic Acid (10)

5 g (25 mmol) of [4-(1,1-dimethoxyethyl)pyrimidin-2-yl]methylamine (9) and 3.85 g of 4-hydrazinobenzoic acid were added, while stirring, to 150 ml of 50% sulfuric acid, and the mixture was heated at 130° C. for 4 h. The methanol which was formed during the reaction was removed continuously from the reaction solution by distillation. After it had been cooled down to 10° C., the reaction mixture was poured onto 200 ml of ice, and the pH was adjusted to about 5.5 using concentrated sodium hydroxide solution. The precipitate of sodium sulfate and product mixture which was formed in this connection was filtered off and the filter residue was extracted several times with methanol. The combined methanol extracts were concentrated and the product was purified by means of flash chromatography (DCM/methanol 9:1). Yield: 0.76 g (11%).

Empirical formula $C_{14}H_{13}N_4O_2$; M.W.=268.28; MS (M+H) 405.2; $^1$H NMR (DMSO-d6) 2.95 (s, 3H), 6.90-7.10 (s(b), 1H), 7.18 (d, J=3 Hz, 1H), 7.4 (s, 1H), 7.58 (d, J=4.5 Hz, 1H), 7.80 (d, J=4.5 Hz, 1H), 8.30 (s, 1H), 7.80 (d, J=4.5 Hz, 1H), 8.38 (d, J=3 Hz, 1H), 11.85 (s, 1H), 12.40-12.60 (s(b), 1H).

A.3.) Bringing the Building Blocks Together and Synthesizing N-[(S)-2-diphenylamino-1-(5-oxo4,5-dihydro-[1,3,4]oxadiazol-2-yl)ethyl]-(2-(2-methylaminopyrimidin-4-yl)-1H-indole-5-carboxamide (13))

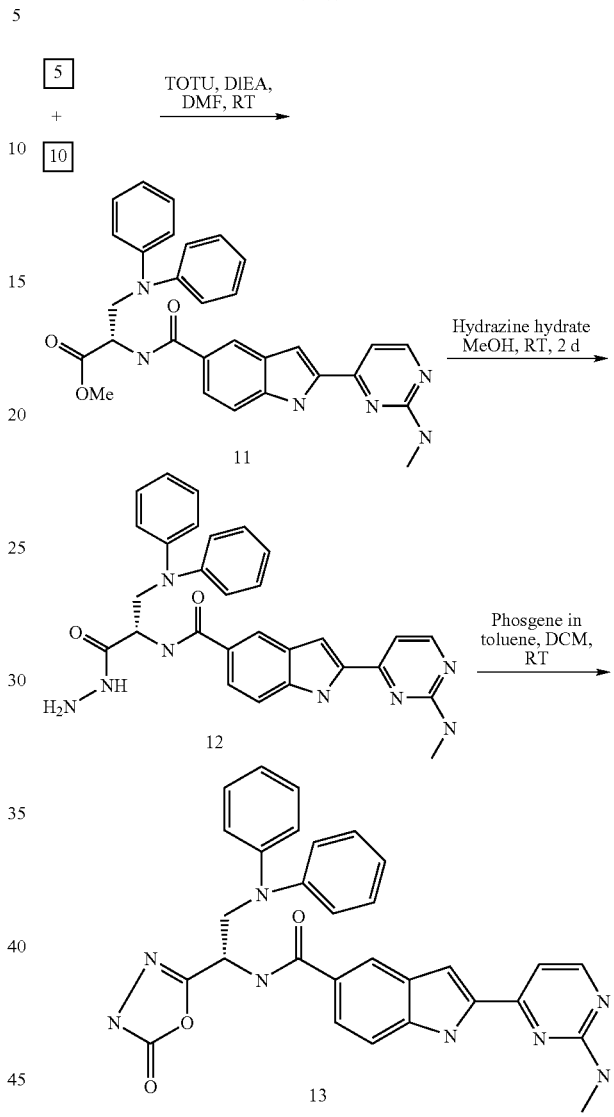

3-Diphenylamino-2-{[2-(2-methylaminopyrimidin4-yl)-1H-indole-5-carbonyl]-(S)-amino}propionic Acid (11)

5.0 g (18.64 mmol) of 2-(2-methylaminopyrimidin4-yl)-1H-indole-5-carboxylic acid (10) were dissolved in 1.2 of DMF, after which 7.9 g (24.08 mmol) of TOTU and 7.9 ml (46.45 mmol) of ethyldiisopropylamine were added consecutively. The mixture was stirred at 5° C. for 20 min. after which 0.73 g (3.28 mmol) of (S)-2-benzyloxycarbonylamino-3-diphenylaminopropionic acid (5) was added to the solution. After 15 h of stirring, the mixture was concentrated under reduced pressure, after which the residue was taken up in n-butanol and the organic phase was extracted with a saturated solution of sodium hydrogen carbonate in order to separate off byproducts. After the organic phase had been dried with $MgSO_4$ and concentrated, the methyl ester of the title compound was isolated by means of flash chromatography on silica gel (DCM:MeOH=19:1). Yield: 4.3 g (98%)

Empirical formula $C_{30}H_{28}N_6O_3$; M.W.=520.22; MS (M+H) 521.3; $^1$H NMR (DMSO-d$_6$) 2.95 (s(b), 3H), 3.60 (s, 3H), 4.19-4.58 (m, 2H), 4.85 (q, 1H), 6.90-7.10 (m, 7H), 7.18 (d, J=3 Hz, 1H), 7.25-7.40 (m, 5H), 7.50 (d, J=4.5 Hz, 1H), 7.65 (d, J=4.5 Hz, 1H), 8.05 (s, 1H), 8.35 (d, J=3 Hz, 1H), 8.70 (d, J=3.75 Hz, 1H), 11.85 (s, 1H).

N-((S)-2-Diphenylamino-1-hydrazinocarbonylethyl)-2-(2-methylaminopyrimidin-4-yl)-1H-indole-5-carboxamide (12)

1.0 g (1.92 mmol) of 3-diphenylamino-2-{[2-(2-methylaminopyrimidin-4-yl)-1H-indole-5-carbonyl]-(S)-amino}propionic acid (11) was dissolved in 10 ml of methanol, after which 0.48 g (9.95 mmol) of hydrazine hydrate was added and the mixture was stirred at room temperature for 15 h. The precipitate of the product (0.3 g) was separated off from the mother liquor by filtration. Further hydrazone 12 (0.1 g) was isolated from the concentrated mother liquor by flash chromatography on silica gel (DCM:MeOH=19:1). Yield: 0.4 g (40%)

Empirical formula $C_{29}H_{28}N_8O_2$; M.W.=520.6; MS (M+H) 521.4; $^1$H NMR (DMSO-d$_6$) 2.95 (s(b), 3H), 4.02-4.58 (m, 2H), 4.4 (s, 2H), 4.85 (q, 1H), 6.90-7.10 (m, 7H), 7.18 (d, J=3 Hz, 1H), 7.20-7.45 (m, 5H), 7.50 (d, J=4.5 Hz, 1H), 7.62 (d, J=4.5 Hz, 1H), 7.99 (s, 1H), 8.25 (d, J=3 Hz, 1H), 8.35 (s(b), 1H), 9.30 (s, 1H), 11.70 (s, 1H).

N-[(S)-2-Diphenylamino-1-(5-oxo-4,5-dihydro-[1,3,4]oxadiazol-2-yl)ethyl]-2-(2-methylaminopyrimidin-4-yl)-1H-indole-5-carboxamide (13)

200 mg (0.384 mmol) of N-((S)-2-diphenylamino-1-hydrazinocarbonylethyl)-2-(2-methylaminopyrimidin-4-yl)-1H-indole-5-carboxamide (12) were suspended in 20 ml of methylene chloride, and a 20% solution of phosgene in toluene (0.398 mmol) was added dropwise at 0° C. and while stirring. The mixture was stirred at room temperature for a further 15 h and the solvent was concentrated. The oxadiazolone 13 was subsequently isolated by flash chromatography on silica gel (DCM:MeOH=9:1). Yield: 160 mg (76%)

Empirical formula $C_{30}H_{26}N_8O_3$; M.W.=546.6; MS (M+H) 547.3; $^1$H NMR (DMSO-d$_6$) 2.95 (s(b), 3H), 4.02-4.58 (m, 2H), 4.85 (q, 1H), 6.90-7.10 (m, 7H), 7.15 (d, J=3 Hz, 1H), 7.20-7.40 (m, 6H), 7.52 (d, J=4.5 Hz, 1H), 7.68 (d, J=4.5 Hz, 1H), 8.10 (s, 1H), 8.92 (d, J=3 Hz, 1H), 11.78 (s, 1H), 12.15-12.40 (s(b), 1H).

B.) Example Benzimidazole IκB-Kinase Inhibitor

B.1.) Synthesis of the Amino Acid (methyl(S)-2-amino-3-diphenylaminopropionate (5)) as Described Under A.1.

B.2.) Synthesis of the Heterocyclic Parent Substance (2-(2-methylaminopyrimidin-4-yl)-1H-benzimidazole-5-carboxylic acid (19))

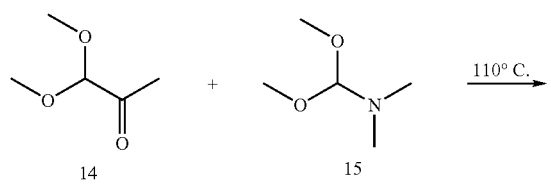

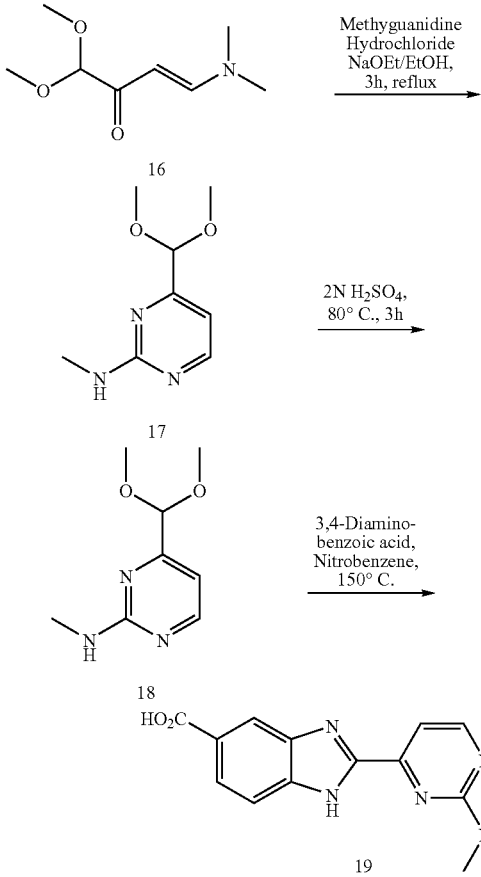

4-Dimethylamino-1,1-dimethoxybut-3-en-2-one (16)

300 g (307 ml, 2.54 mol) of methylglyoxal dimethylacetal were stirred, at 110° C. for 4 hours (h), with 303 g (337 ml, 2.54 mol) of N,N-dimethylformamide dimethylacetal. The methanol which was formed during the reaction was removed continuously from the reaction solution by distillation. After having been cooled down, the solution was extracted with heptane and the solvents were evaporated. This resulted in 303 g of crude product 16 (yield 70%), which was reacted without any further purification.

Empirical formula $C_8H_{15}NO_3$; M.W.=173.21; MS (M+H) 174.1; $^1$H NMR (DMSO-d$_6$) 2.10 (s, 1H), 2.80 (s, 3H), 3.10 (s, 3H), 3.25 (s, 3H), 3.3 (s, 3H), 4.42 (s, 1H), 5.19 (d(b), J=12.8 Hz, 1H), 7.60 (d, J=15 Hz, 1H).

(4-Dimethoxymethylpyrimidin-2-yl)methylamine (17)

0.33 g (14.4 mmol) of sodium was dissolved in 50 ml of absolute ethanol. 1.57 g (14.4 mmol) of methylguanidine hydrochloride and 2.48 g (14.4 mmol) of 4-dimethylamino-1,1-dimethoxybut-3-en-2-one (16) were added, while stirring, to the solution, which was heated at boiling heat for 3 h. In order to terminate the reaction, the ethanol was evaporated. The resulting product 17 was used without any further purification. Yield: 2.6 g (quantitative).

Empirical formula $C_8H_{13}N_3O_2$; M.W.=183.21; MS (M+H) 184.1; $^1$H NMR (DMSO-d$_6$) 2.78 (s, 6H), 3.10 (s, 3H), 5.02 (s, 1H), 6.62 (d, J=3 Hz, 1H).

2-Methylaminopyrimidine-4-carbaldehyde (18)

10 g (54 mmol) of (4-dimethoxymethylpyrimidin-2-yl)methylamine (17) were dissolved in 54 ml of 2N sulfuric acid and the solution was heated at 80° C. for 3 h while being stirred. After the reaction had cooled down, the reaction solution was carefully brought to a pH of about 9 using solid $Na_2CO_3$ and extracted 3 times with ethanol. After the solvent had been evaporated, the combined dried extracts yielded the title aldehyde 18 in 60% yield (4.47 g)

Empirical formula $C_6H_7N_3O$; M.W.=137.12; MS (M+H) 138.2; $^1$H NMR (DMSO-$d_6$) 2.60-2.80 (s(b), 3H), 6.95 (d, J=3 Hz, 1H), 7.40-7.60 (s(b), 8.55 (d, J=3 Hz, 1H).

2-(2-Methylaminopyrimidin4-yl)-1H-benzimidazole-5-carboxylic acid (19)

4.3 g (31.3 mmol) of methylaminopyrimidine-4-carbaldehyde (18) and 4.8 g (31.1 mmol) of 3,4-diaminobenzoic acid were heated at 150° C. for 2 h in 300 ml of nitrobenzene. After the mixture had been cooled down to 0° C., the precipitate of the benzimidazole was separated off from the nitrobenzene by filtration and the product was purified by flash chromatography (DCM/methanol 4:1). Yield: 2.66 g (32%)

Empirical formula $C_{13}H_{11}N_5O_2$; M.W.=269.28; MS (M+H) 270.2; $^1$H NMR (DMSO-$d_6$) 2.95 (s, 3H), 7.50 (d, J=3 Hz, 1H), 7.75 (d, J=4.5 Hz, 1H), 7.90 (d, J=4.5 Hz, 1H), 8.35 (s, 1H), 8.55 (d, J=3 Hz, 1H), 8.70-9.05 (s(b), 1H).

3.) Bringing the Building Blocks Together and Synthesizing N-((S)-1-carbamoyl-2-diphenylaminoethyl)-2-(2-methylaminopyrimidin-4-yl)-1H-benzimidazole-5-carboxamide (22)

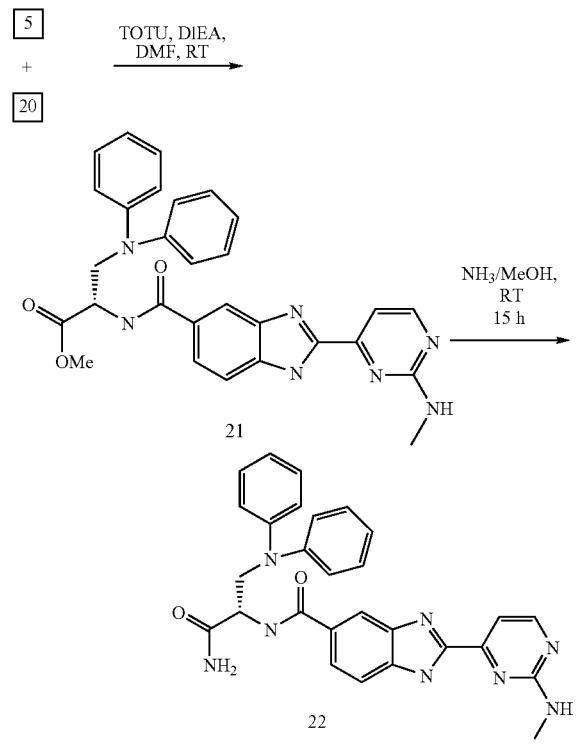

3-Diphenylamino-2-{[2-(2-methylaminopyrimidin-4-yl)-1H-benzimidazole-5-carbonyl]-(S)-amino}propionic Acid (21)

2.6 g (9.6 mmol) of 2-(2-methylaminopyrimidin-4-yl)-1H-benzimidazole-5-carboxylic acid (20) were dissolved in 300 ml of DMF, after which 3.17 g (9.6 mmol) of TOTU and 1.6 ml (11.6 mmol) of ethyldiisopropylamine were added consecutively. The solution was stirred at 5° C. for 20 min, after which 2.6 g (9.6 mmol) of (S)-2-benzyloxycarbonylamino-3-diphenylamino-propionic acid (5) were added to it. After 16 h of stirring, the mixture was concentrated under reduced pressure, after which the methyl ester 21 was isolated by means of flash chromatography on silica gel (DCM:MeOH=9:1).

Yield: 1.61 g (32%) Empirical formula $C_{29}H_{27}N_7O_3$; M.W.=521.58; MS (M+H) 522.3; $^1$H NMR (DMSO-$d_6$) 2.95 (s(b), 3H), 3.60 (s, 3H), 4.19-4.40 (m, 2H), 4.90 (q, 1H), 6.90-7.10 (m, 6H), 7.25-7.35 (m, 6H), 7.40 (d, J=4.5 Hz, 1H), 7.60-7.80 (d(b) 1H), 8.05-8.25 (d(b), 1H), 8.45 (d, J=3 Hz, 1H), 8.90 (s(b), 1H), 11.85 (s(b), 1H).

N-((S)-1-Carbamoyl-2-diphenylaminoethyl)-2-(2-methylaminopyrimidin-4-yl)-1H-benzimidazole-5-carboxamide (22)

50 ml of (absolute) methanol were saturated with ammonia at 0° C. 0.5 g (0.959 mmol) of 3-diphenylamino-2-{[2-(2-methylaminopyrimidin4-yl)-1H-benzimidazole-5-carbonyl]-(S)-amino}propionic acid (21) was added to this mixture and the whole was stirred at room temperature for 24 h. After the solvent and excess ammonia had been evaporated, the amide 22 was isolated by flash chromatography on silica gel (DCM:MeOH=19:1). Yield: 0.43 g (89%)

Empirical formula $C_{29}H_{28}N_8O_2$; M.W.=506.57; MS (M+H) 507.2; $^1$H NMR (DMSO-$d_6$) 2.95 (s(b), 3H), 4.02-4.35 (m, 2H), 4.85 (q, 1H), 6.80-7.10 (m, 6H), 7.15-7.25 (m, 5H), 7.40 (d, J=4.5 Hz, 1H), 7.58 (s(b), 1H), 7.68 (s(b), 1H), 8.06-8.19 (d(b), 1H), 8.40-8.58 (m, 2H), 13.10 (s, 1H).

EXPERIMENTAL

Pharmacological Examples

IκB-Kinase ELISA:

The activity of the IκB-kinase was determined using an ELISA which comprised a biotinylated substrate peptide, which contained the amino acid sequence in the IκB protein from serine 32 to 36, and a specific polyclonal or monoclonal antibody (e.g. from New England Biolabs, Beverly, Mass., USA, Cat.: 9240), which only bound to the phosphorylated form of the IκB peptide. This complex was immobilized on an antibody-binding (protein A-coated) plate and detected using a conjugate 30 composed of a biotin-binding protein and HRP (e.g. streptavidin-HRP). The activity was quantified with the aid of a standard curve constructed using substrate phosphopeptide.

Implementation:

In order to obtain the kinase complex, 10 ml of HeLa S3 cell extract S100 were diluted with 40 ml of 50 mM HEPES, pH 7.5, brought to 40% with respect to ammonium sulfate and incubated on ice for 30 minutes. The precipitated pellet was dissolved in 5 ml of SEC buffer (50 mM HEPES, pH 7.5, 1 mM DTT, 0.5 mM EDTA, 10 mM 2-glycerophosphate), centrifuged at 20 000 g for 15 minutes and filtered through a 0.22 µm filter. The sample was loaded onto a 320 ml Superose-6 FPLC column (Amersham Pharmacia Biotech AB, Uppsala, Sweden) which had been equilibrated with SEC buffer and which was operated at 4° C. with a flow rate of 2 ml/min. The fractions which were located at the migration time of the 670 kDa molecular weight standard were combined for the activation. Activation was achieved by means of a 45-minute incubation with 100 nM MEKK1Δ, 250 µM MgATP, 10 mM $MgCl_2$, 5 mM dithiothreitol (DTT), 10 mM 2-glycerophosphate and 2.5 µM microcystin-LR at 37° C. The activated enzyme was stored at −80° C. The test substances (2 µl), which were dissolved in DMSO, were preincubated, at 25° C. for 30 minutes, with 43 µl of activated enzyme (diluted 1:25 in reaction buffer 50 mM HEPES, pH 7.5, 10 mM $MgCl_2$, 5 mM DTT, 10 mM β-glycerophosphate, 2.5 µM microcystin-LR). 5 µl of substrate peptide (biotin-$(CH_2)_6$-DRHDS-GLDSMKD-$CONH_2$) (200 µM) were then added, after which the mixture was incubated for one hour and the reaction was stopped with 150 µl of 50 mM HEPES, pH 7.5, 0.1% BSA, 50 mM EDTA, antibody [1:200]. 100 µl of the stopped reaction mixture or of a standard phosphopeptide dilution series (biotin-$(CH_2)_6$-DRHDS[$PO_3$]GLDSMKD-$CONH_2$) were then transferred to a protein A plate (Pierce Chemical Co., Rockford, Ill., USA), after which the plate was incubated for 2 hours while being shaken. After 3 washing steps with PBS, 100 µl of 0.5 µg/ml streptavidin-HRP (horseradish peroxidase) (diluted in 50 mM HEPES/0.1% BSA) were added for 30 minutes. After 5 washing steps with PBS, 100 µL of TMB substrate (Kirkegaard & Perry Laboratories, Gaithersburg, Md., USA) were added and the color development was stopped by adding 100 µL of 0.18 M sulfuric acid. The absorption was measured at 450 nm. The standard curve was produced by linear regression corresponding to a 4-parameter dose-effect relationship. This standard curve was used to quantify the enzyme activity or its inhibition by the test substances.

The $IC_{50}$ for N-[(S)-2-diphenylamino-1-(5-oxo-4,5-dihydro[1,3,4]oxadiazol-2-yl)ethyl]-2-(2-methylaminopyrimidin-4-yl)-1H-indole-5-carboxamide was 0.050 µM.

The $IC_{50}$ for N-((S)-1-carbamoyl-2-diphenylaminoethyl)-2-(2-methylaminopyrimidin-4-yl)-1H-benzimidazole-5-carboxamide was 0.045 µM.

Pain Assay

The analgesic and antinociceptive activity of the compound N-[(S)-2-diphenylamino-1-(5-oxo-4,5-dihydro[1,3,4]oxadiazol-2-yl)ethyl]-2-(2-methylaminopyrimidin-4-yl)-1H-indole-5-carboxamide, termed compound 13 in that which follows, was demonstrated in the two following models:

$1^{st}$ model: Zymosan-induced paw inflammation in the rat;
  Parameter: paw withdrawal time or paw withdrawal threshold during thermal or mechanical stimulation of the hind paw.
$2^{nd}$ model: Kaolin/carrageenan-induced knee joint inflammation in the rat;
  Parameter: reaction of spinal neurons during pressure stimulation of the knee.

Model 1

Experimental implementation: in short-term anesthesia using isoflurane, 1 mg of Zymosan (as a suspension in 100 µl of PBS (phosphate-buffered salt solution)) was injected subcutaneously into the middle of the plantar side of one of the experimental animal's hind paws. After that, two different behavioral tests were used to quantitatively determine the development of a hyperalgesia.

a) Determining the Paw Withdrawal Time during Thermal Stimulation (Hargreaves Test).

The experimental animal was placed in a transparent plastic chamber having a glass floor. As soon as the experimental animal was no longer moving, following the reconnaissance phase (about 5 min), an infrared light source was positioned directly below the hind paw to be stimulated and switched on. The lamp emitted focused infrared light of increasing intensity, such that the skin temperature of the hind paw increased almost linearly. As soon as the animal withdrew the paw, the lamp switched itself off. The temperature of the paw at the time it is withdrawn has just become unpleasant for the animal; this is referred to as the thermal pain threshold.

b) Determining the paw withdrawal threshold during mechanical stimulation (von Frey test) The experimental animal was placed in a transparent plastic chamber whose floor consisted of wire-gauze. Punctate pressure of defined strength was produced using calibrated nylon fibers, what are termed von Frey hairs. The weakest pressure stimulation during which the animal withdrew its paw determines the mechanical pain threshold.

About half an hour before, and at various times after, the Zymosan injection, the thermal and mechanical pain thresholds were determined on the right hind paw and on the left hind paw (see Tables 1, 2). The decrease in the ipsilateral pain threshold, expressed in % of the contralateral pain threshold, was then calculated (see Tables 1, 2). The degree of hyperalgesia is directly proportional to the magnitude of this decrease.

In a control group, the Zymosan injection induced pronounced mechanical and thermal hyperalgesia (see control data in Tabs. 1 and 2). In another group of animals, which were under short-term isoflurane anesthesia, the abovementioned compound 13 was injected intraperitoneally (i.p.) (in each case 30 mg/kg in polyethylene glycol/water mixture (PEG/water 1:1) about 15 minutes before, and 2.5 and 5.5 hours after Zymosan injection. From two hours after Zymosan injection onward, the thermal hyperalgesia was less pronounced in these animals than it was in the control group; after the third administration of the substance, it was no longer possible to observe any side difference at all in the paw withdrawal time (Tab. 1). In addition, this effect still persisted for 18 hrs after the last administration of the substance.

Compound 13 also significantly reduced the mechanical hyperalgesia. The effect set in 1 hour after Zymosan injection and also still persisted 18 hrs after the last administration of the substance (see Tab. 2).

The activity of compound 13 is very strong in both test models. Comparative data from a study which was carried out previously show that compound 13 reduces the thermal hyperalgesia considerably more powerfully than does the NSAID diclofenac.

TABLE 1

Change in the paw withdrawal time (%)

| Time (h) after Zymosan injection (0) | Mean value Compound 13 | SD compound 13 | Mean value control | SD control |
|---|---|---|---|---|
| Baseline-0.5 | 0.0 | 0.0 | 0.0 | 0.0 |
| 0.5 | −16.6 | 6.6 | −21.4 | 6.3 |
| 1 | −31.3 | 14.1 | −28.8 | 11.6 |
| 2 | −30.2 | 15.4 | −44.8 | 19.1 |

TABLE 1-continued

Change in the paw withdrawal time (%)

| Time (h) after Zymosan injection (0) | Mean value Compound 13 | SD compound 13 | Mean value control | SD control |
|---|---|---|---|---|
| 3 | −15.3 | 5.3 | −49.2 | 17.9 |
| 4 | −16.0 | 11.5 | −50.6 | 23.0 |
| 5 | −9.7 | 18.6 | −46.6 | 24.8 |
| 6 | 5.0 | 2.6 | −38.4 | 17.6 |
| 7 | 3.4 | 5.8 | −29.9 | 22.1 |
| 24 | −3.8 | 7.0 | −46.1 | 18.4 |

TABLE 2

Change in the paw withdrawal threshold (%)

| Time (h) after Zymosan injection (0) | Mean value Compound 13 | SD compound 13 | Mean value control | SD control |
|---|---|---|---|---|
| Baseline-0.5 | 0.0 | 0.0 | 0.0 | 0.0 |
| 0.5 | −37.4 | 6.6 | −48.9 | 31.3 |
| 1 | −43.1 | 20.5 | −66.0 | 23.2 |
| 2 | −36.0 | 17.8 | −71.8 | 26.0 |
| 3 | −35.1 | 13.1 | −60.5 | 20.2 |
| 4 | −46.7 | 11.9 | −64.3 | 18.2 |
| 5 | −40.6 | 14.0 | −55.5 | 25.8 |
| 6 | −33.1 | 23.3 | −57.3 | 18.0 |
| 7 | −44.7 | 21.5 | −47.1 | 23.9 |
| 24 | −9.7 | 26.6 | −41.5 | 17.3 |

Model 2,

Experimental implementation: In rats which were under sodium thiopental anesthesia, the spinal canal was opened and spinal medullary neurons which processed the "pain impulses" from the knee-joint were identified. Following identification, a long-term recording, in which the activity of the nerve cell was recorded before and during the development of an acute inflammation in the knee-joint, was carried out. For this, the responses to non-noxious and noxious stimulation at the knee-joint were measured in a control period before inducing the inflammation and for several hours after inducing the inflammation.

The acute inflammation was induced by the intraarticular injection of a suspension (about 150 μl) of kaolin and carrageenan. In controlled experiments, only the vehicle was applied to the spinal medullary surface in order to represent the development of the hyperexcitability under control conditions. As a rule, this development of hyperexcitability took place within 2 to 4 hours and was expressed in a marked increase in the responses to non-noxious and noxious stimulation of the knee-joint (Tab. 3). In the experiments in which the abovementioned compound 13 was applied, the substance was added (about 30 μl of a 10 μM solution) to the spinal medulla about 30 minutes before inducing the inflammation. The responses of the cell to non-noxious and noxious stimulation were then subsequently monitored as in the control experiments.

Comparison of the changes in the responses in the two groups shows that, as compared with the controls, compound 13 almost completely suppressed the development of spinal hyperexcitability (Tab. 3). Taken overall, the effect of compound 13 on the responses to noxious knee-joint stimulation was more strongly expressed than was the effect of indomethacin, as was shown by a comparison with published data from an earlier study.

TABLE 3

Neuronal responses before and during knee-joint inflammation (imp/15 s)

| Time (min) after K/C injection | Mean value Compound 13 | SEM compound 13 | Mean value control | SEM control |
|---|---|---|---|---|
| Noxious stimulation at the knee-joint | | | | |
| Baseline | 0.8 | 29.9 | 0 | 0 |
| 30-60 | 62.3 | 49.3 | 161.6 | 43.7 |
| 60-120 | 26.9 | 35 | 458.1 | 125.4 |
| 120-180 | 8.5 | 58.9 | 544.2 | 140.0 |
| 180-240 | 19.5 | 59.9 | 616.3 | 174.7 |
| Non-noxious stimulation at the knee-joint | | | | |
| Baseline | 0.92 | 16.90 | 0 | 0 |
| 30-60 | 8.66 | 23.76 | 21.4 | 11.9 |
| 60-120 | 2.71 | 25.94 | 74.6 | 38.3 |
| 120-180 | 11.16 | 24.22 | 105.7 | 39.0 |
| 180-240 | 39.78 | 25.09 | 149.7 | 44.3 |

The effect of N-((S)-1-carbamoyl-2-diphenylaminoethyl)-2-(2-methylaminopyrimidin-4-yl)-1H-benzimidazole-5-carboxamide, termed compound 22 below, was also tested in model 2.

Control Data: see Table 3

TABLE 4

Neuronal responses before and during knee-joint inflammation (imp/15 s)

| Time (min) after K/C injection | Compound 22 Experiment 1 | Compound 22 Experiment 2 |
|---|---|---|
| Noxious stimulation at the knee-joint | | |
| Baseline | 0 | 0 |
| 30-60 | −109.1 | −9.2 |
| 60-120 | −101.1 | |
| 120-180 | −37.8 | 60 |
| 180-240 | | 96.7 |
| Non-noxious stimulation at the knee-joint | | |
| Baseline | 0 | 0 |
| 30-60 | −34.1 | −30.6 |
| 60-120 | −37.2 | |
| 120-180 | −32.1 | 50.3 |
| 180-240 | | 68.7 |

The data verify the good effect of compound 22 in model 2.

3rd Model: Zymosan-Induced Paw Inflammation in the Mouse;

Parameter: Paw Withdrawal Time during Thermal Stimulation of the Hind Paw. Experimental implementation: In short-term anesthesia using isoflurane, 25 μl of a suspension containing 50 mg of zymosan/ml were injected into the right hind paw of the experimental animal. The development of a hyperalgesia was then determined quantitatively as follows:

Determining the Paw Withdrawal Time during Thermal Stimulation (Hargreave's Test; see above).

The experimental animal was placed in a transparent plastic chamber having a glass floor. As soon as the experimental animal was no longer moving, following the reconnaissance phase (about 5 min), an infrared light source was positioned directly below the hind paw to be stimulated and switched on. The lamp emitted focused infrared light of increasing intensity such that the skin temperature of the hind paw increased almost linearly. As soon as the animal withdrew the paw, the lamp switched itself off. The temperature of the paw at the time it is withdrawn has just become unpleasant for the animal; this is referred to as the thermal pain threshold.

Shortly before the zymosan injection, and for from 7 to 14 days after the injection, the thermal pain threshold was determined once daily on the right hind paw and left hind paw. Subsequently, the integral of the area which was formed from the curves for the paw withdrawal times of the inflamed paw and the noninflamed paw (AUC, area between the curves, see tables 5 and 6) was determined as a measure of the hyperalgesia. The larger this value is, the more pronounced is the hyperalgesia, and the smaller the value is in animals which are being given the substance, the greater is the success of the therapy.

In a 7-day study, the zymosan injection induced pronounced thermal hyperalgesia in a control group (see vehicle, tab. 5). In the other groups, the substance was administered for the first time one day after the zymosan injection, after marked thermal hyperalgesia had already developed. Compound 13 was then administered orally twice daily for 7 days, in each case at the rate of 25 or 75 mg/kg in HEC/lipofundin (1% HEC in lipofundin). Analysis of the paw withdrawal times during the entire period of the study (7 days) showed that, when the substance was administered, the AUC decreased in a dose-dependent manner. At single doses of from 8.3 mg/kg and upwards, a significant therapeutic effect was achieved as compared with the vehicle group (tab. 5). Compound 13 exhibits very strong activity in the test model. A very high dose of paracetamol was likewise administered twice daily to another group of animals which was taken through the experiment in parallel. Compound 13 reduced the thermal hyperalgesia to a greater extent than did paracetamol (tab. 5).

TABLE 5

Thermal hyperalgesia during the seven days following zymosan injection

|  | AUC mean value [measure of hyperalgesia] | Standard error of the arithmetic mean (SEM) | Number of animals per group | Statistical difference as compared with the vehicle |
|---|---|---|---|---|
| Vehicle | 45.1 | 1.5 | 8 |  |
| Paracetamol, 200 mg/kg | 24.6 | 4.1 | 8 | yes |
| Compound 13, 2.8 mg/kg | 40.4 | 2.4 | 8 | no |
| Compound 13, 8.3 mg/kg | 32.3 | 2.2 | 8 | yes |
| Compound 13, 25 mg/kg | 19.4 | 2.9 | 8 | yes |
| Compound 13, 75 mg/kg | 17.4 | 2.6 | 8 | yes |

In another study carried out on mice, the activity of compound 13 was compared with that of the specific COX-2 inhibitor Celecoxib. The scheme for zymosan injection and dosing was identical to that in the previously described study. The only difference was that this additional study ran for 14 days.

Once again, compound 13 was able to reduce thermal hyperalgesia in a dose-dependent manner (tab. 6). In the experiment, compound 13 and Celecoxib had equally strong effects at the high dosage (tab. 6).

TABLE 6

Thermal hyperalgesia during the 14 days following zymosan injection

|  | AUC mean value [measure of hyperalgesia] | Standard error of the arithmetic mean (SEM) | Number of animals per group | Statistical difference as compared with the vehicle |
|---|---|---|---|---|
| Vehicle | 90.0 | 5.1 | 8 |  |
| Celecoxib, 8.3 mg/kg | 79.9 | 5.9 | 5 | no |
| Celecoxib, 25 mg/kg | 51.5 | 3.7 | 9 | no |
| Compound 13, 8.3 mg/kg | 64.5 | 5.0 | 5 | yes |
| Compound 13, 25 mg/kg | 47.6 | 4.4 | 9 | yes |

4th Model: Zymosan-Induced Paw Inflammation in the Mouse;

Parameter: Spontaneous Running Performance in a Running Wheel. In the cage in which it is kept, the experimental animal has access to a running wheel, the revolutions of which are recorded electronically. During the night hours, the C57/B6 mice use the running wheel voluntarily and, after a one-week phase of acclimatization, cover on average 4 100 meters/night. After zymosan has been injected, the distance run each night is reduced. This reduction in running performance is a valid parameter for a restriction in function which is due to inflammation pain. Experimental implementation: After an acclimatization phase of one week, the distance run/24 hours was measured in order to determine the base line. 25 μl of a suspension containing 50 mg of zymosan/ml were then injected into the right hind paw of the experimental animal during short-term anesthesia using isoflurane. The distance run/24 hours was then determined during the following seven days. In the analysis, the area under the curve for the values for the distance run was determined (AUC, tab. 7): the lower the AUC, the lower was the running performance during the week following injection of the zymosan. Compound 13 was administered twice daily for 7 days, with the dose in each case being 25 or 75 mg/kg in HEC/lipofundin (1% HEC in lipofundin). The substance was administered for the first time on day 1 after injection of the zymosan.

In one study, the effect of compound 13 on running performance following zymosan injection was compared with that of paracetamol. A dose-dependent increase in the distance run, which was significant as compared with the vehicle group, was found in the case of both the higher doses (tab. 7). By contrast, no improvement as compared with the vehicle group was achieved when paracetamol was used at an extremely high dose (also 2 □ daily) (tab. 7).

TABLE 7

Running wheel activity during the seven days following zymosan injection

|  | AUC mean value | Standard error of the arithmetic mean (SEM) | Number of animals per group | Statistical difference as compared with the vehicle |
|---|---|---|---|---|
| Vehicle | 108.8 | 12.5 | 8 |  |
| Paracetamol, 200 mg/kg | 187.2 | 42.7 | 8 | no |
| Compound 13, 2.8 mg/kg | 131.1 | 23.3 | 8 | no |
| Compound 13, 8.3 mg/kg | 142.1 | 29.1 | 8 | no |
| Compound 13, 25 mg/kg | 216.7 | 58.5 | 8 | yes |
| Compound 13, 75 mg/kg | 251.7 | 41.9 | 8 | yes |

We claim:
1. A method for treating pain in a patient in need thereof, comprising administering to the patient a pharmaceutically effective amount of an IκB-kinase inhibitor of the compound of formula Ia:

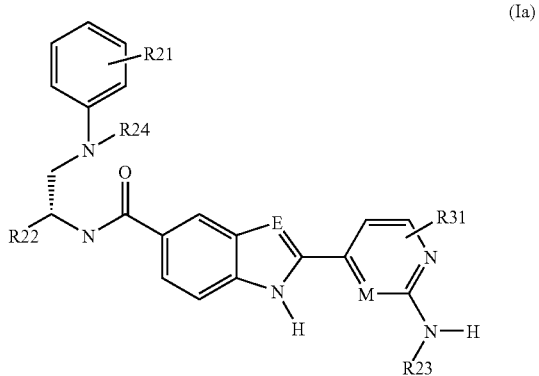

or a stereoisomeric form thereof or a mixture of stereoisomeric forms in any ratio, or a physiologically tolerated salt thereof, wherein, E is CH;
M is N;
R21 is hydrogen,
halogen,
—($C_1$-$C_4$)-alkyl,
—CN,
—$CF_3$,
—$OR^{15}$, wherein, $R^{15}$ is hydrogen or —($C_1$-$C_4$)-alkyl,
—$N(R^{15})$—$R^{16}$ wherein, $R^{15}$ and $R^{16}$ are, independently of each other, hydrogen or
—($C_1$-$C_4$)-alkyl,
—C(O)—$R^{15}$, wherein, $R^{15}$ is hydrogen or —($C_1$-$C_4$)-alkyl, or
—S(O)$_x$—$R^{15}$, wherein, x is zero, 1 or 2, and $R^{15}$ is hydrogen or —($C_1$-$C_4$)-alkyl;
R31 is hydrogen,
halogen,
—($C_1$-$C_4$)-alkyl,
—CN,
—$CF_3$,
—$OR^{15}$, wherein, $R^{15}$ is hydrogen atom or —($C_1$-$C_4$)-alkyl,
—$N(R^{15})$—$R^{16}$ wherein, $R^{15}$ and $R^{16}$ are, independently of each other, hydrogen or —($C_1$-$C_4$)-alkyl,
—C(O)—$R^{15}$, wherein, $R^{15}$ is hydrogen or —($C_1$-$C_4$)-alkyl, or
—S(O$_x$—$R^{15}$, wherein, x is zero, 1 or 2, and $R^{15}$ is hydrogen or —($C_1$-$C_4$)-alkyl;
R22 is a heteroaryl radical selected from 3-hydroxypyrro-2,4-dione, imidazole, imidazolidine, imidazoline, indazole, isothiazole, isothiazolidine, isoxazole, 2-isoxazolidine, isoxazolidine, isoxazolone, morpholine, oxazole, 1,3,4-oxadiazole, oxadiazolidinedione, oxadiazolone, 1,2,3,5-oxathiadiazole-2-oxide, 5-oxo-4,5-dihydro-[1,3,4]oxadiazole, 5-oxo-1, 2,4-thiadiazole, piperazine, pyrazine, pyrazole, pyrazoline, pyrazolidine, pyridazine, pyrimidine, tetrazole, thiadiazole, thiazole, thiomorpholine, triazole and triazolone, wherein the heteroaryl radical is optionally substituted one, two or three times by —C(O)—$R^{15}$, wherein $R^{15}$ is hydrogen or —($C_1$-$C_4$)-alkyl, —($C_1$-$C_4$)-alkyl, —O—$R^{15}$, wherein $R^{15}$ is hydrogen or —($C_1$-$C_4$)-alkyl, —$N(R^{15})$—$R^{16}$, wherein $R^{15}$ and $R^{16}$ are, independently of each other, hydrogen or —($C_1$-$C_4$)-alkyl, halogen, or a keto radical,
—C(O)—$R^{15}$, wherein $R^{15}$ is hydrogen or —($C_1$-$C_4$)-alkyl,
—C(O)—$OR^{15}$, wherein $R^{15}$ is hydrogen or —($C_1$-$C_4$)-alkyl, or
—C(O)—$N(R^{17})$—$R^{18}$, wherein $R^{17}$ and $R^{18}$ are, independently of each other,
hydrogen,—($C_1$-$C_4$)—alkyl—OH,—O—($C_1$-$C_4$)-alkyl or —($C_1$-$C_4$)-alkyl;
R23 is hydrogen or —($C_1$-$C_4$)-alkyl; and
R24 is a heteroaryl radical selected from pyrrole, furan, thiophene, imidazole, pyrazole, oxazole, isoxazole, thiazole, isothiazole, tetrazole, 1,2,3,5-oxathiadiazole-2-oxide, triazolones, oxadiazolones, isoxazolones, oxadiazolidinedione, tfiazole, 3-hydroxypyrro-2,4-dione, 5-oxo-1,2,4-thiadiazole, pyridine, pyrazine, pyrimidine, indole, isoindole, indazole, phthalazine, quinoline, isoquinoline, quinoxaline, quinazoline, cinnoline, β-carboline and benzo fused cyclopenta derivatives or cyclohexa derivatives of these heteroaryl radicals, wherein the heteroaryl radical is optionally substituted, one, two or three times, independently of each other, by —($C_1$-$C_5$)-alkyl, —($C_1$-$C_5$)-alkoxy, halogen, nitro, amino, trifluoromethyl, hydroxyl, hydroxy—($C_1$-$C_4$)-alkyl, methylenedioxy, ethylenedioxy, formyl, acetyl, cyano, hydroxycarbonyl, aminocarbonyl or —($C_1$-$C_4$)-alkoxycarbonyl, or an aryl radical selected from phenyl, naphthyl, 1-naphthyl, 2-naphthyl, biphenylyl, 2-biphenylyl, 3-biphenylyl and 4-biphenylyl, anthryl and fluorenyl, wherein the aryl radical is optionally substituted, one, two or three times independently of each other, by —($C_1$-$C_5$)-alkyl, —($C_1$-$C_5$)-alkoxy, halogen, nitro, amino, trifluoromethyl, hydroxyl, hydroxy—($C_1$-$C_4$)-alkyl, methylenedioxy, ethylenedioxy, formyl, acetyl, cyano, hydroxycarbonyl, aminocarbonyl or —($C_1$-$C_4$)-alkoxycarbonyl wherein, the pain is an acute pain selected from a group consisting of a pain following injury, a post operative pain, a pain associated with an acute attack of gout, and an acute pain following jaw-bone surgical intervention.

2. The method according to claim 1, wherein, for formula Ia,
E is CH;
M is N;
R21 is hydrogen, halogen,
—($C_1$-$C_4$)-alkyl,
—CN,
—$CF_3$,
—$OR^{15}$, wherein, $R^{15}$ is hydrogen atom or —($C_1$-$C_4$)-alkyl,
—$N(R^{15})$—$R^{16}$ wherein, $R^{15}$ and $R^{16}$ are, independently of each other, hydrogen or
—($C_1$-$C_4$)-alkyl,
—C(O)—$R^{15}$, wherein, $R^{15}$ is hydrogen or —($C_1C_4$)-alkyl, or
—S(O)$_x$—$R^{15}$, wherein, x is zero, 1 or 2, and $R^{15}$ is hydrogen or —($C_1$-$C_4$)-alkyl;
R22 is a heteroaryl radical selected from imidazole, isothiazole, isoxazole, 2-isoxazolidine, isoxazolidine, isoxazolone, 1,3,4-oxadiazole, oxadiazolidinedione, 1,2,3,5-oxadiazolone, oxazole, 5-oxo-4,5-dihydro[1,3,4]oxadiazole, tetrazole, thiadiazole, thiazole, triazole and triazolone, wherein the heteroaryl radical is optionally substituted one, two or three times by a keto radical, halogen, or —($C_1$-$C_2$)-alkyl,
—C(O)—$N(R^{17})$—$R^{18}$, wherein $R^{17}$ and $R^{18}$ are hydrogen,—($C_1$-$C_2$)-alkyl —OH, —O—($C_1$-$C_2$)-alkyl, or —($C_1$-$C_4$)-alkyl;
R23 is hydrogen, methyl or ethyl;

R24 is a heteroaryl radical selected from unsaturated, partially saturated and completely saturated rings which are derived from pyridine, pyrazine, pyrimidine, pyridazine, pyrrole, furan, thiophene, imidazole, pyrazole, oxazole, isoxazole, thiazole, triazole or isothiazole, wherein the heteroaryl radical is optionally substituted, one, two or three times, independently of each other by —($C_1$-$C_4$)-alkyl, —($C_1$-$C_4$)-alkoxy, F, Cl, I, Br, nitro, amino, trifluoromethyl, hydroxyl, hydroxy—($C_1$-$C_4$)-alkyl, methylenedioxy, ethylenedioxy, formyl, acetyl, cyano, hydroxycarbonyl, aminocarbonyl or—($C_1$-$C_4$-alkoxycarbonyl, or phenyl, wherein, the phenyl is optionally substituted one, two or three times, independently of each other, by F, Cl, I, Br, $CF_3$, —OH, —($C_1$-$C_4$)-alkyl or ($C_1$-$C_4$)-alkoxy; and R31 is hydrogen, halogen, —($C_1$-$C_4$)-alkyl,

—CN,

—$CF_3$,

—$OR^{15}$, wherein, R15 is hydrogen atom or —($C_1$-$C_4$)-alkyl,

—$N(R^{15})$—$R^{16}$ wherein, $R^{15}$ and $R^{16}$ are, independently of each other, hydrogen or —($C_1$-$C_4$)-alkyl, —$C(O)$—$R^{15}$, wherein, $R^{15}$ is hydrogen or —($C_1$-$C_4$)-alkyl, or —$S(O)_x$—$R^{15}$, wherein, x is zero, 1 or 2, and $R^{15}$ is hydrogen or —($C_1$-$C_4$)-alkyl.

3. The method according to claim 1, wherein the compound of formula Ia is, wherein the compound N-[(S)-2-diphenylamino-1-(5-oxo-4,5-dihydro[1,3,4]oxadiazol-2-yl)ethyl]-2-(2-methylaminopyrimidin-4-yl)-1H-indole-5-carboxamide.

* * * * *